US011931517B2

(12) United States Patent
Palmieri

(10) Patent No.: US 11,931,517 B2
(45) Date of Patent: Mar. 19, 2024

(54) GERMICIDAL UV LIGHT DEVICE

(71) Applicant: Herman David Palmieri, Pittsburgh, PA (US)

(72) Inventor: Herman David Palmieri, Pittsburgh, PA (US)

( * ) Notice: Subject to any disclaimer, the term of this patent is extended or adjusted under 35 U.S.C. 154(b) by 0 days.

(21) Appl. No.: 18/120,795

(22) Filed: Mar. 13, 2023

(65) Prior Publication Data

US 2023/0293844 A1 Sep. 21, 2023

Related U.S. Application Data

(60) Provisional application No. 63/320,498, filed on Mar. 16, 2022.

(51) Int. Cl.
| | |
|---|---|
| *A61M 16/10* | (2006.01) |
| *A61K 39/215* | (2006.01) |
| *A61L 9/18* | (2006.01) |
| *A61M 16/00* | (2006.01) |
| *A61M 16/06* | (2006.01) |
| *C07K 14/165* | (2006.01) |

(52) U.S. Cl.
CPC ........... *A61M 16/10* (2013.01); *A61K 39/215* (2013.01); *A61L 9/18* (2013.01); *A61M 16/0045* (2013.01); *A61M 16/06* (2013.01); *A61M 16/1055* (2013.01); *C07K 14/165* (2013.01); *A61L 2209/12* (2013.01)

(58) Field of Classification Search
CPC .... A61M 16/10; A61M 16/105; A61M 16/06; A61M 16/0045; A61M 16/0003; A61M 16/08; A61M 16/1055; A61M 16/106; A61M 16/1065; A61M 16/107; A61M 2202/30; A61K 39/215; C07K 14/165; A61L 9/18; A61L 2209/12
See application file for complete search history.

(56) References Cited

U.S. PATENT DOCUMENTS

| 8,757,154 B2* | 6/2014 | Schuller | ............ A61M 16/0063 128/205.27 |
|---|---|---|---|
| 11,452,793 B1* | 9/2022 | Fulbrook | ................. A61L 9/205 |
| 2007/0163588 A1* | 7/2007 | Hebrank | ........... A61M 16/0069 128/205.29 |
| 2011/0232645 A1* | 9/2011 | Smith | ............... A61M 16/0816 128/205.23 |

(Continued)

*Primary Examiner* — Colin W Stuart

(57) ABSTRACT

A device for capturing momentarily an exhaled breath of a COVID 19 patient containing active SARS-CoV-2 virions within an accessible compartment of said device and converting said active SARS-CoV-2 virions into far-UVC inactivated SARS-CoV-2 virions by exposure to an activated 222 nm far-UVC lamp mounted in said accessible compartment and with the next inhaled breath of said COVID 19 patient said far-UVC inactivated SARS-CoV-2 virions are positioned within the respiratory system ready to be captured by an antigen-presenting cells such as the Dendritic cells (DCs) which are antigen-presenting cells that capture, process, and present antigens to lymphocytes to initiate and regulate the adaptive immune response. Said far-UVC inactivated SARS-CoV-2 virions can be collected from said accessible compartment of said device and processed into viable vaccine that can be administered to front-line workers.

9 Claims, 21 Drawing Sheets

(56) References Cited

U.S. PATENT DOCUMENTS

| | | | | |
|---|---|---|---|---|
| 2016/0271288 A1* | 9/2016 | Davis | .................. | A61M 16/107 |
| 2018/0001049 A1* | 1/2018 | Schuller | ............. | B01D 53/0415 |
| 2020/0368468 A1* | 11/2020 | Liu | ........................ | G16H 20/40 |
| 2021/0308407 A1* | 10/2021 | Fitzgerald | ............ | A62B 18/025 |
| 2021/0330850 A1* | 10/2021 | Catalan | ................... | A61L 9/122 |
| 2022/0395605 A1* | 12/2022 | Zhao | .................... | A62B 18/025 |

* cited by examiner

GERMICIDAL UV LIGHT DEVICE

CROSS-REFERENCE TO RELATED APPLICATIONS

This application claims the benefit of prior-filed, U.S. Provisional Patent Application No. 63/320,498, filed on Mar. 16, 2022, the contents of which are incorporated herein by reference in their entirety.

BACKGROUND OF THE INVENTION

The present invention relates to a device and method using a concealed activated far-UVC Lamp that instantly creates a far-UVC inactivated SARS-CoV-2 virions from the exhaled breath of a COVID-19 patient. Said far-UVC Lamp completely inactivates the SARS-CoV-2 virions infectivity while preserving its morphology, antigenic properties, and the ability to induce the production of virus-neutralizing antibodies. When said far-UVC inactivated SARS-CoV-2 virions are inhaled by said COVID-19 patient the Dendritic cells (DCs) capture, process, and present said far-UVC inactivated SARS-CoV-2 virions to the lymphocytes to initiate and regulate the adaptive immune response which for some is a lifesaving event.

Although the far-UVC 222 nm Germicidal lamp is able to deactivate many types of virus particles successfully and it is safe enough to be used in the presence of humans. There is no prior art that exists when it comes to the creation of purpose, design and functionality of this present invention entitled the Germicidal UV Light Device which includes the use of a far-UVC 222 nm Germicidal lamp. In short, there is no prior art to compare it with.

SUMMARY OF THE PRESENT INVENTION

The present invention proposes a device and method that momentarily captures the exhaled breath of a COVID-19 patient containing infectious active virions within an accessible compartment of said device in which a far-UVC Lamp is mounted, activated, and instantly converts active SARS-CoV-2 virions to far-UVC inactivated SARS-CoV-2 virions. Within seconds said far-UVC inactivated SARS-CoV-2 virions are inhaled by said COVID-19 patient into the respiratory system of said COVID-19 patient where they are captured and presented, thereby triggering the adaptive immune system which is vital to clearing the SARS-CoV-2 virus. Unlike said active SARS-CoV-2 virions which are able to resist or delay the Dendritic cells (DCs) from capturing them, said far-UVC inactivated SARS-CoV-2 virions do not fight or resist T cells or said Dendritic cells. Said far-UVC inactivated SARS-CoV-2 virions and said active SARS-CoV-2 virions are identical in structure. These facts enable said Dendritic cells to easily capture and present said far-UVC inactivated SARS-CoV-2 virions to the lymphocytes which result in the initiation and regulation of the adaptive immune response. Thus producing the most effective and preferred antibodies.

COVID-19 caused by the SARS-CoV-2 virus continues to cause globally significant impacts on public health. SARS-CoV-2 is related to other coronaviruses such as the Middle East Respiratory Syndrome Coronavirus (MERS-CoV) and SARS-CoV all of which cause respiratory infections in humans. SARS-CoV-2 triggered a global public health emergency and continues to have a major impact socially, culturally, and economically. Vaccination is believed to be the most effective way to negate the SARS-CoV-2 pandemic, but there is another type of vaccination that is not included in this statement and may be proven to be the only type of vaccination that will negate the SARS-CoV-2 pandemic and that vaccination is instantly created and instantly administered by the UV Germicidal Light Device 410.

In a recent study it was found the number of total T cells, $CD4^+$ and $CD8^+$ T cells were dramatically reduced in said COVID-19 patients, especially in patients requiring to be held in an Intensive Care Unit (ICU) care. These T cells were found to appear functionally exhausted. In some said COVID-19 patients, it is apparent that said SARS-CoV-2 virus is capable of overpowering the immune system of an infected COVID-19 patient thereby impairing the immune system's ability to produce antibodies. For some, their immune system is able to clear said SARS-CoV-2 virus. For others whose immune system is not able to clear said SARS-CoV-2 virus they will most likely experience a fatal outcome. Therefore, early activation of the immune system is paramount to the survival of a person infected with said SARS-CoV-2 virus. There is no way to know at an early enough stage of infection as to whose immune system will clear said SARS-CoV-2 virus and whose immune system will not. The safest thing for a COVID-19 infected person to do is to begin treatments with the Germicidal UV Light Device 410 as soon as you know that you have become infected with said SARS-CoV-2 virus, COVID-19.

In addition there are several methods, such as, a method of vetting a COVID-19 patient for treatment; a method of use in the administration of a consecutive breathing treatment; a method of use in the administration of an intermittent breathing treatment; a method in the creation and collection of far-UVC Inactivated SARS-CoV-2 virions; a method to make ready for use; a method of administering a subsequent five minute Consecutive Breathing Treatment; a method of administering a subsequent five minute said Intermittent Breathing Treatment; and a method of use in the creation and administration of a far-UVC SARS-CoV-2 virions for complete antibody production are all essential in the operation of said Germicidal UV Light Device. Said Germicidal UV Light Device and aforementioned methods are not intended to be limited for treatment of said SARS-CoV-2 virus/COVID-19 patients but can be used to inactivated other viruses and bacteria.

DETAILED DESCRIPTION OF THE PREFERRED EMBODIMENTS

Figure 1:
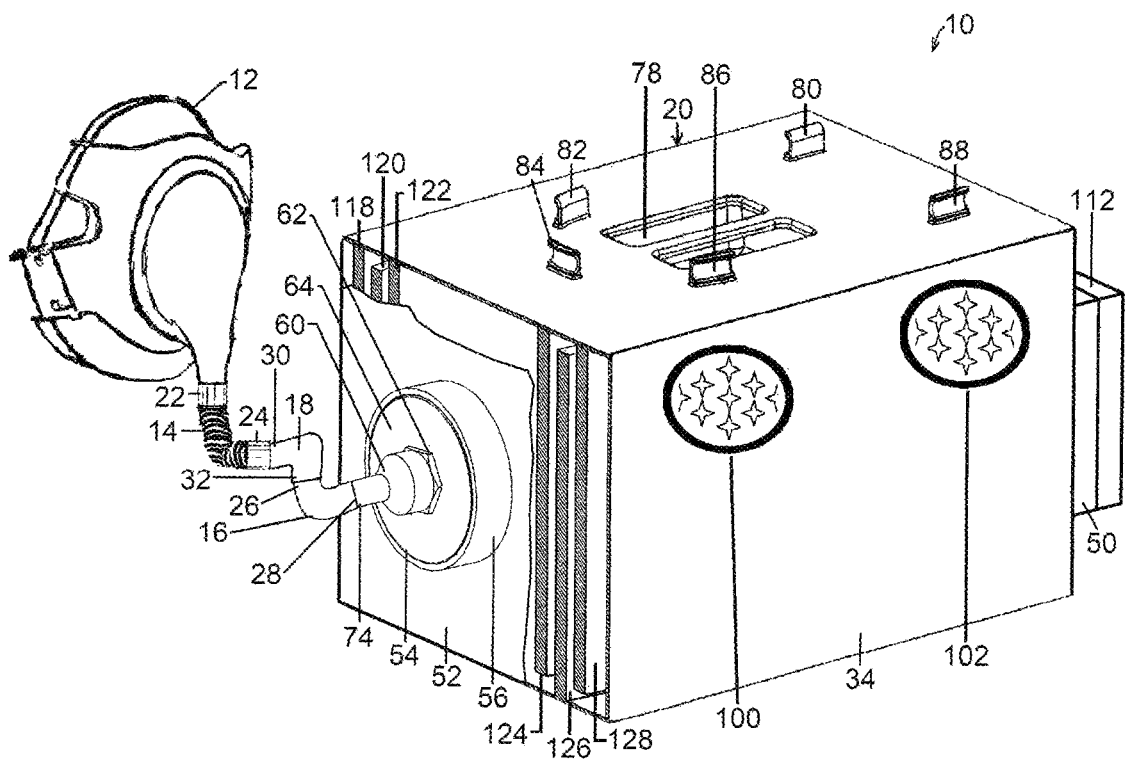
FIG. 1 is a tilted cut away view of the Germicidal UV Light Device.

In a Preferred Embodiment, the Germicidal UV Light Device 10 comprises a mask 12 having an unrestricted bidirectional air passageway, a flexible hose 14, a first removable right-angle connector 16 a second removable right-angle connector 18 and a vented container 20, as shown in FIG. 1. Said mask 12 fully covers the mouth and both of the nostril areas. Said flexible hose 14 includes a first connector 22 and a second connector 24, as shown in FIG. 1. Said first removable right-angle connector 16 includes first end 26 and second end 28, as shown in FIG. 1. Said second removable right-angle connector 18 includes first end 30 and second end 32, as shown in FIG. 1. Said first connector 22 is connected to said mask 12. Said second connector 24 is affixed to said first end 30 of said second removable right-angle connector 18, as shown in FIG. 1. Said second end 32 of said second removable right-angle connector 18 is affixed to said first end 26 of first removable right-angle connector 16, as shown in FIG. 1.

Figure 2:
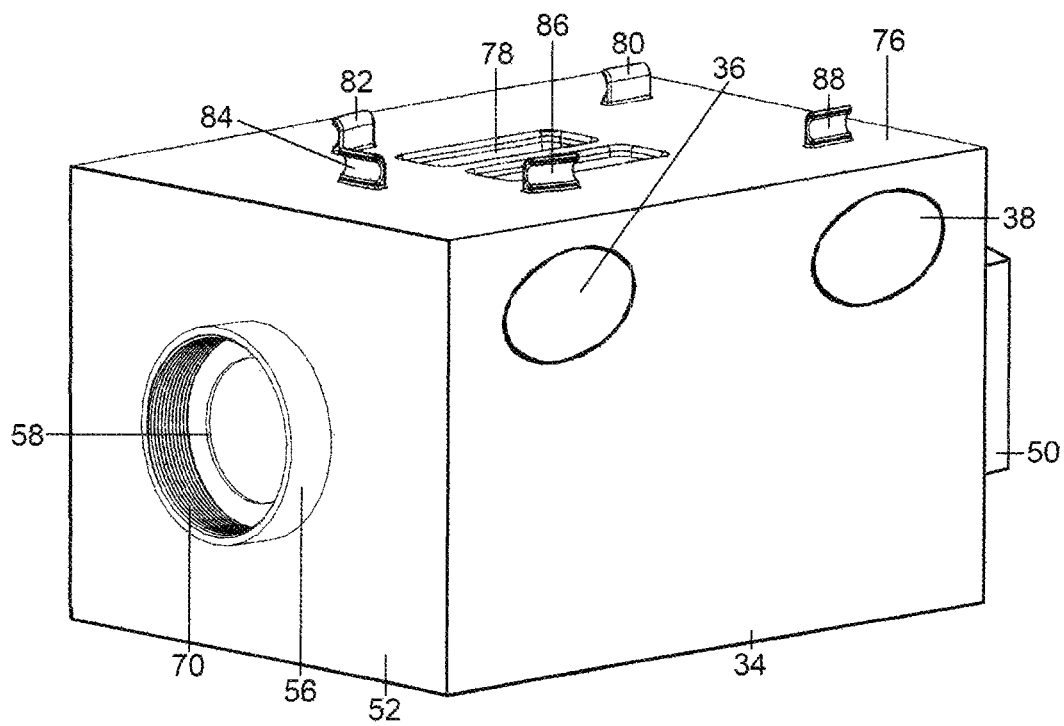
FIG. 2 is an unassembled tilted view of the Germicidal UV Light Device.
Figure 3:
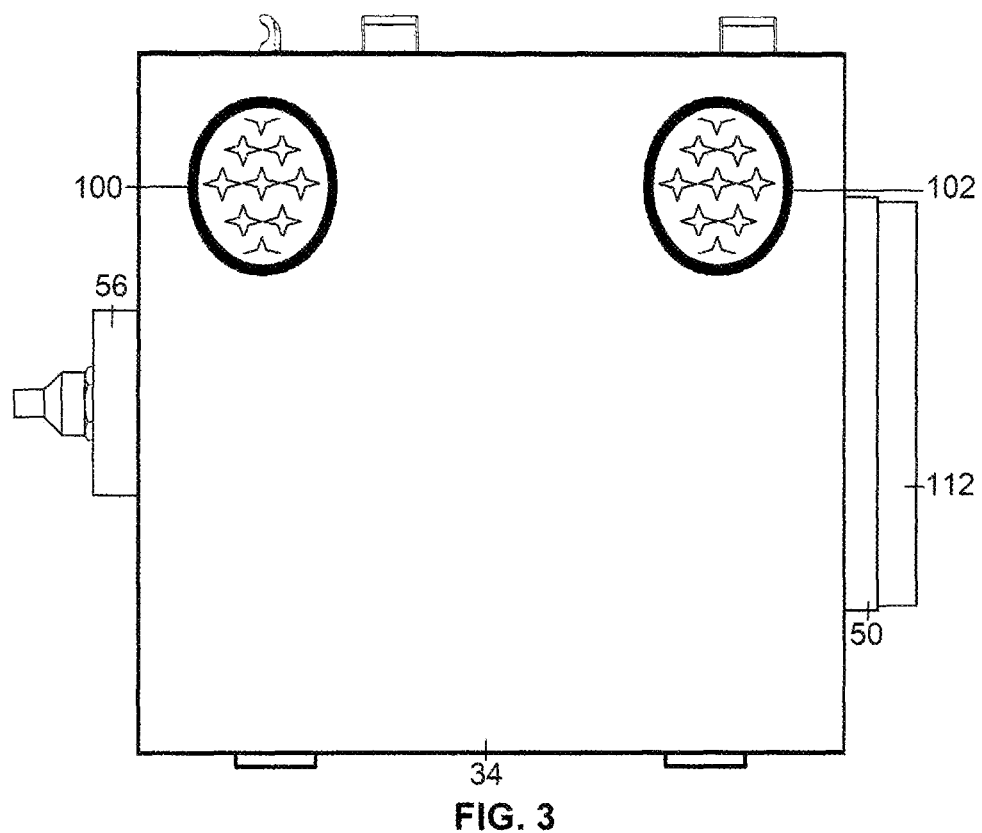
FIG. 3 is a front wall view of the Germicidal UV Light Device.
Figure 4:
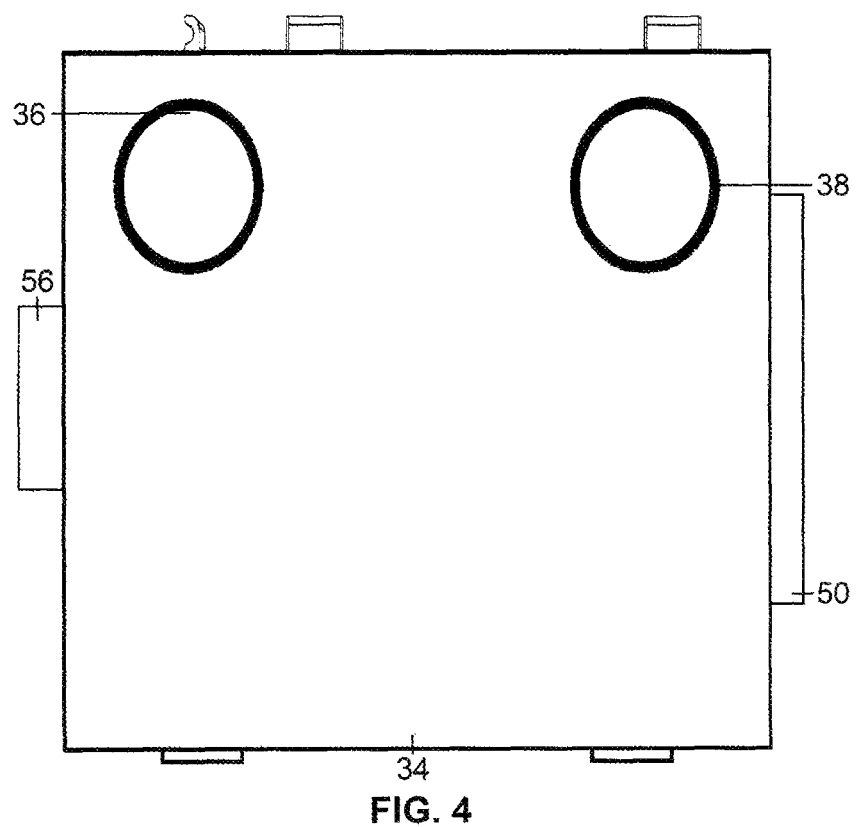
FIG. 4 is an unassembled front wall view of the Germicidal UV Light Device.
Figure 5:
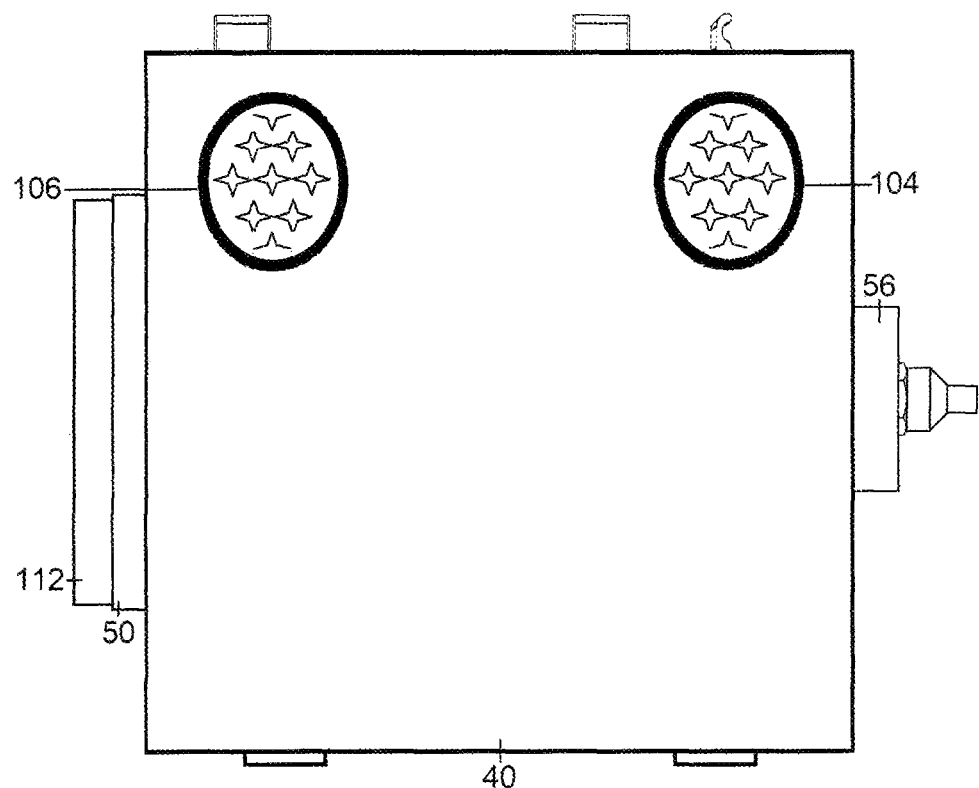
FIG. 5 is a rear wall view of the Germicidal UV Light Device.
Figure 6:
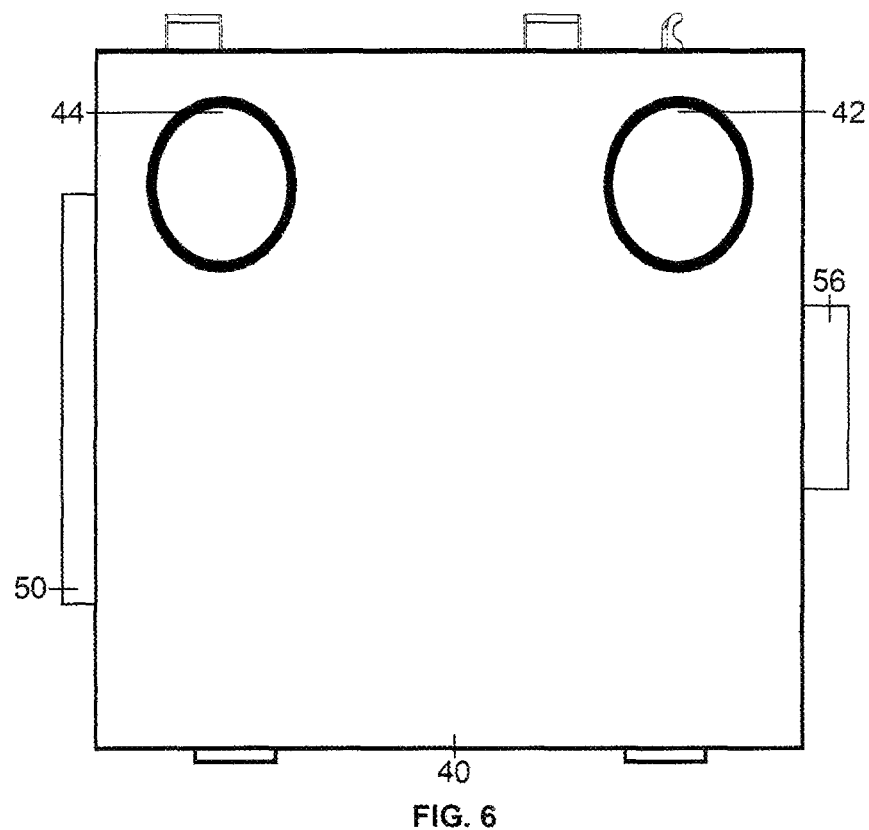
FIG. 6 is an unassembled rear wall view of the Germicidal UV Light Device.
Figure 7:
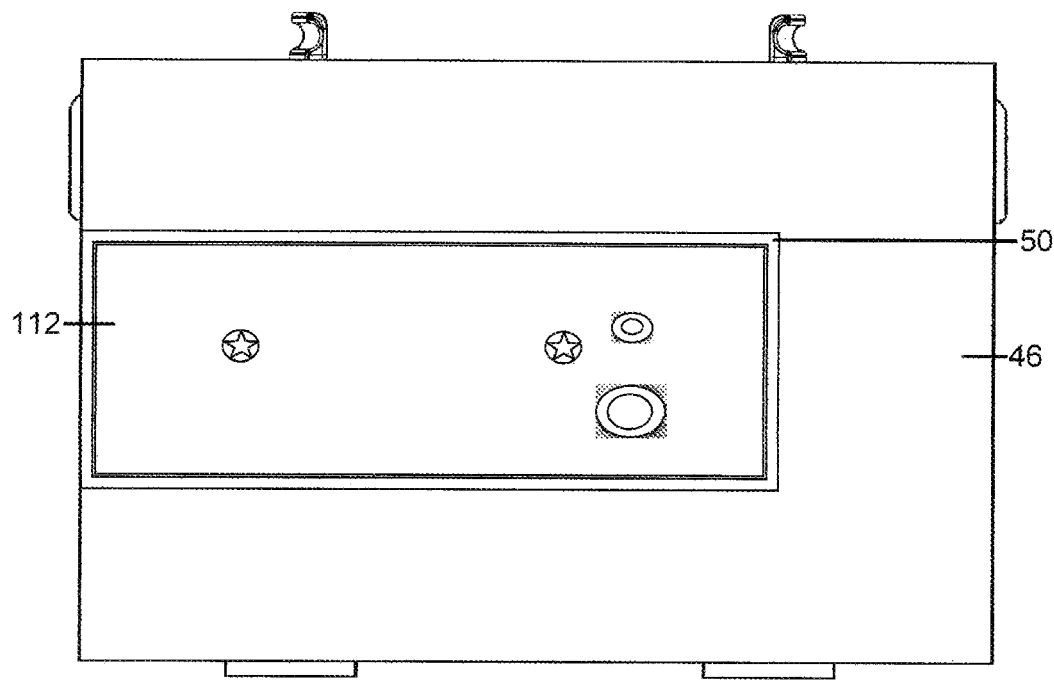
FIG. 7 is a right outside wall view of the Germicidal UV Light Device.
Figure 8:
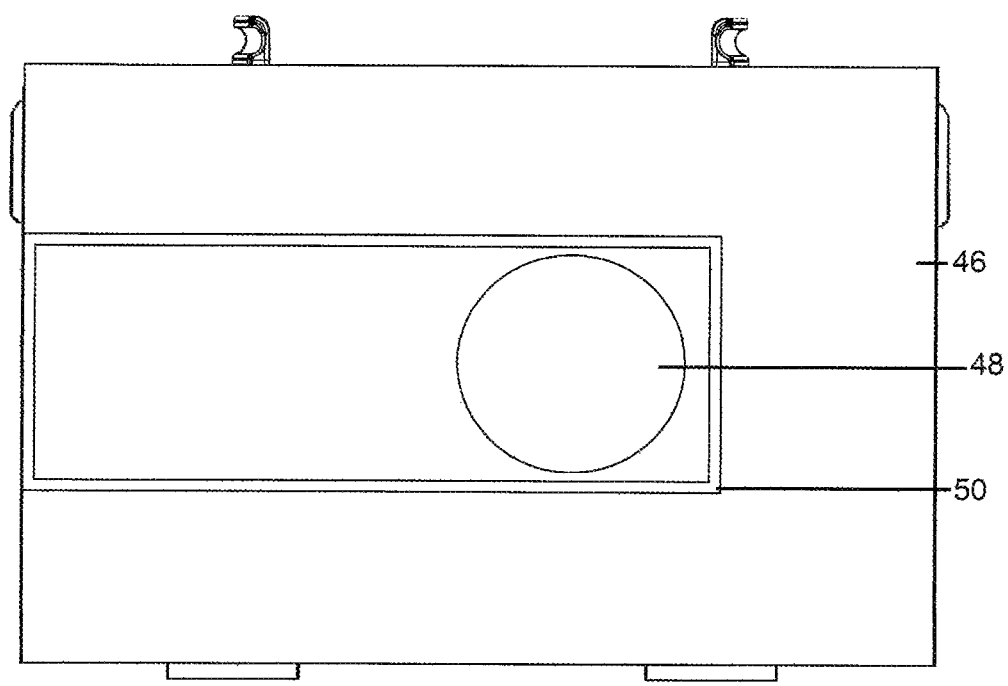
FIG. 8 is an unassembled right outside wall view of the Germicidal UV Light Device.
Figure 9:
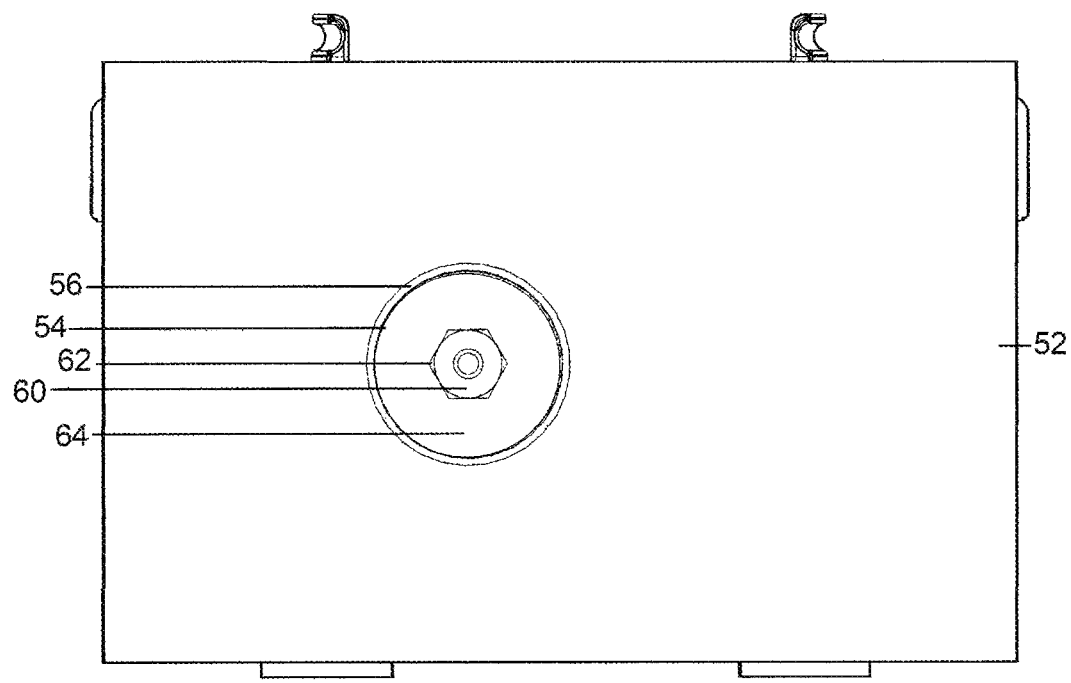
FIG. 9 is a left outside wall view of the Germicidal UV Light Device.
Figure 10:
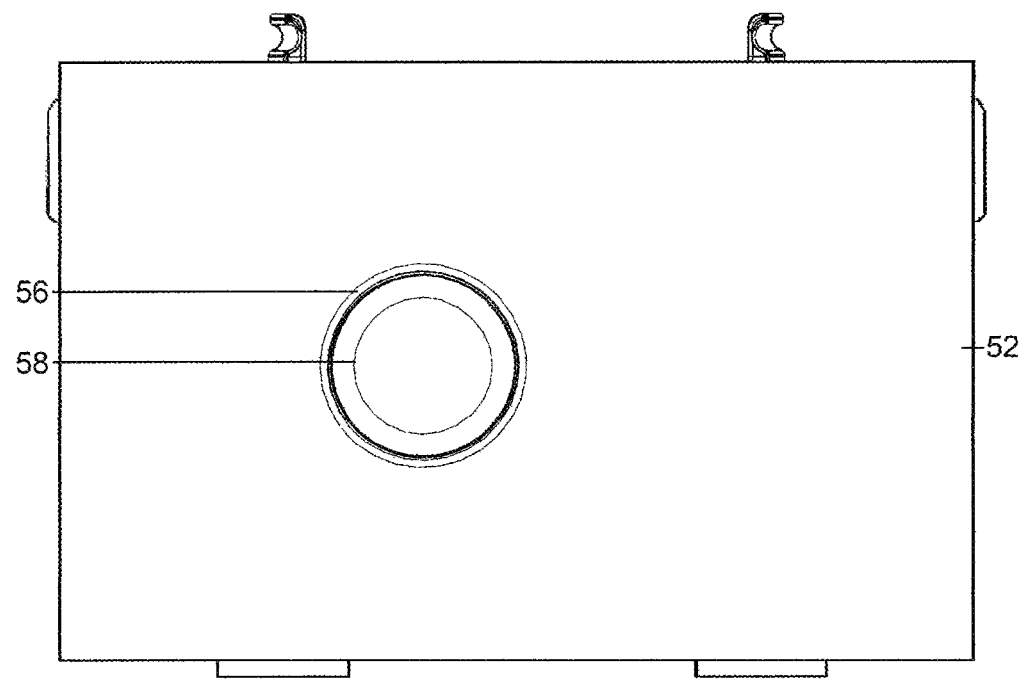
FIG. 10 is an unassembled left outside wall view of the Germicidal UV Light Device.
Figure 11:
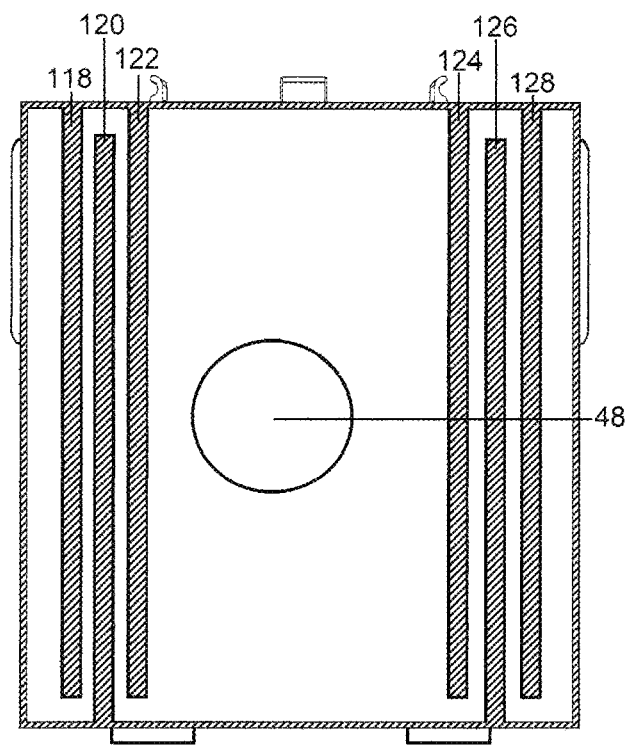
FIG. 11 is an unassembled left side cut away view of the Germicidal UV Light Device.
Figure 12:
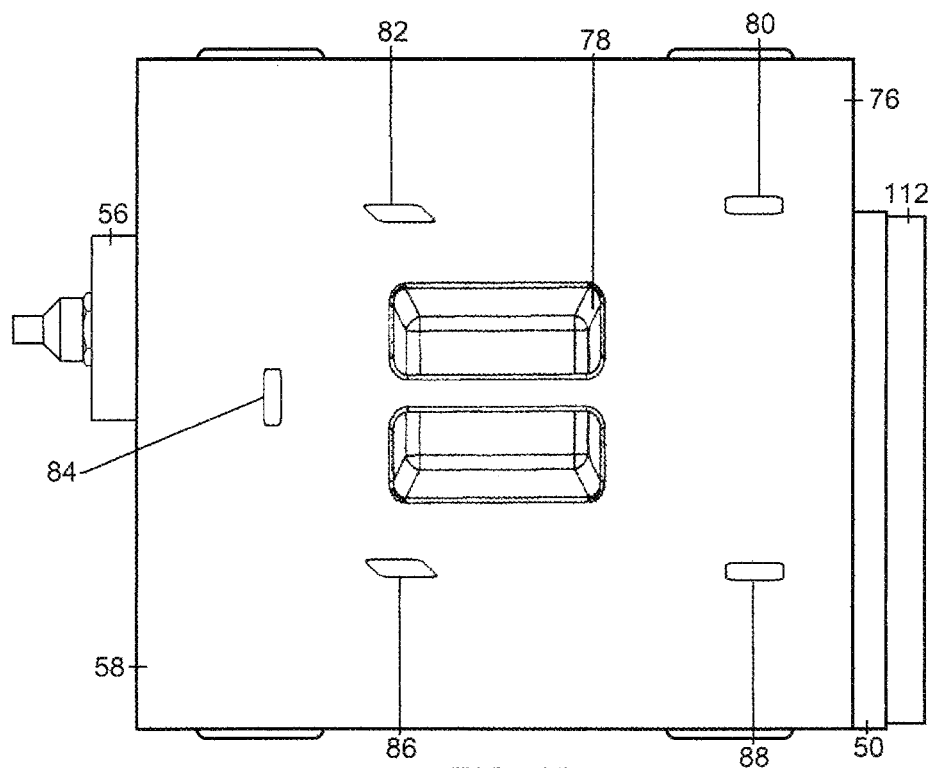
FIG. 12 is a top view of the Germicidal UV Light Device.
Figure 15:
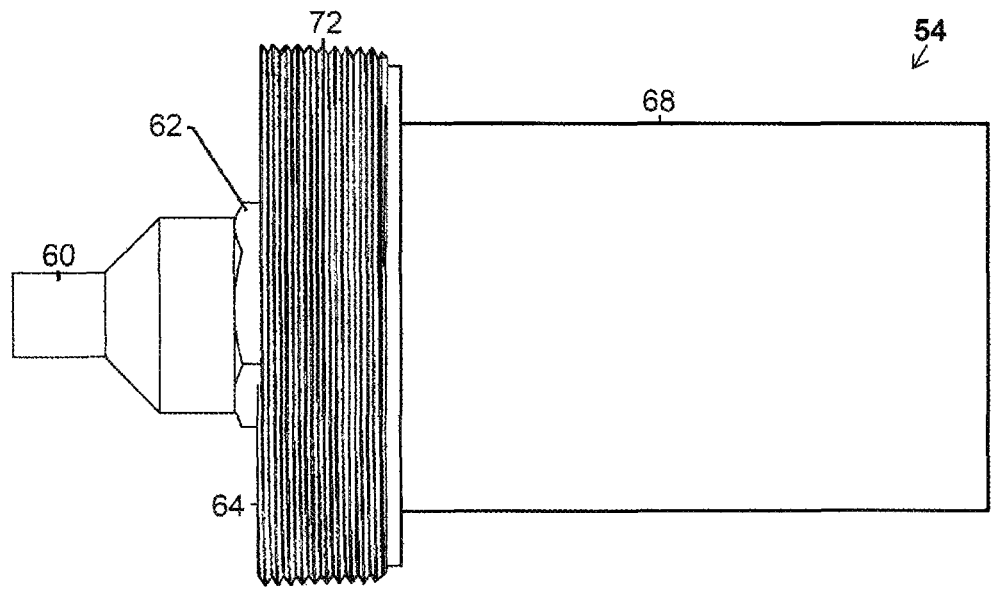
FIG. 15 is a right side view of the removable hose inlet of the Germicidal UV Light Device.
Figure 16:
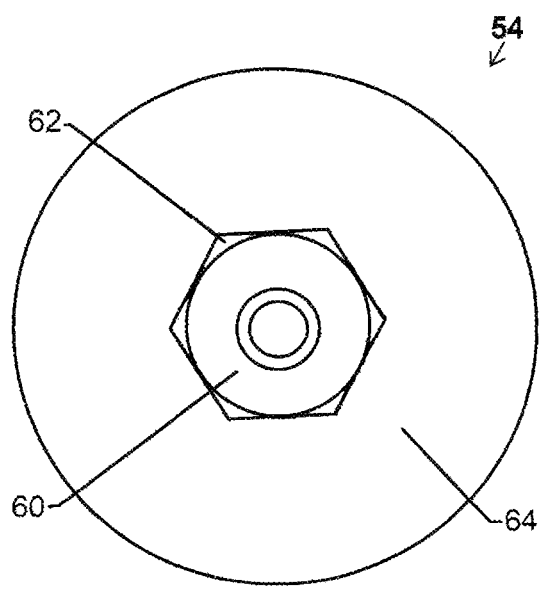
FIG. 16 is a front view of the removable hose inlet of the Germicidal UV Light Device.
Figure 17:
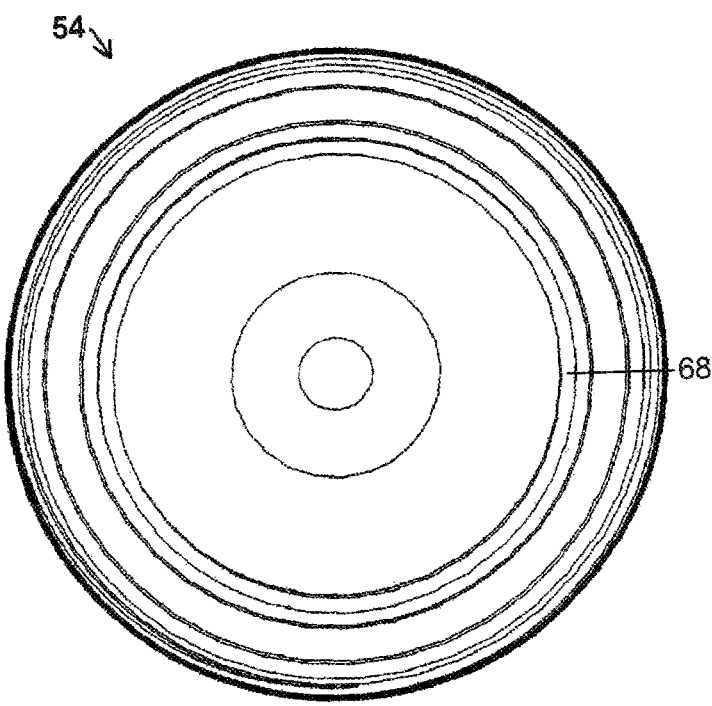
FIG. 17 is a back view of the removable hose inlet of the Germicidal UV Light Device.
Figure 18:
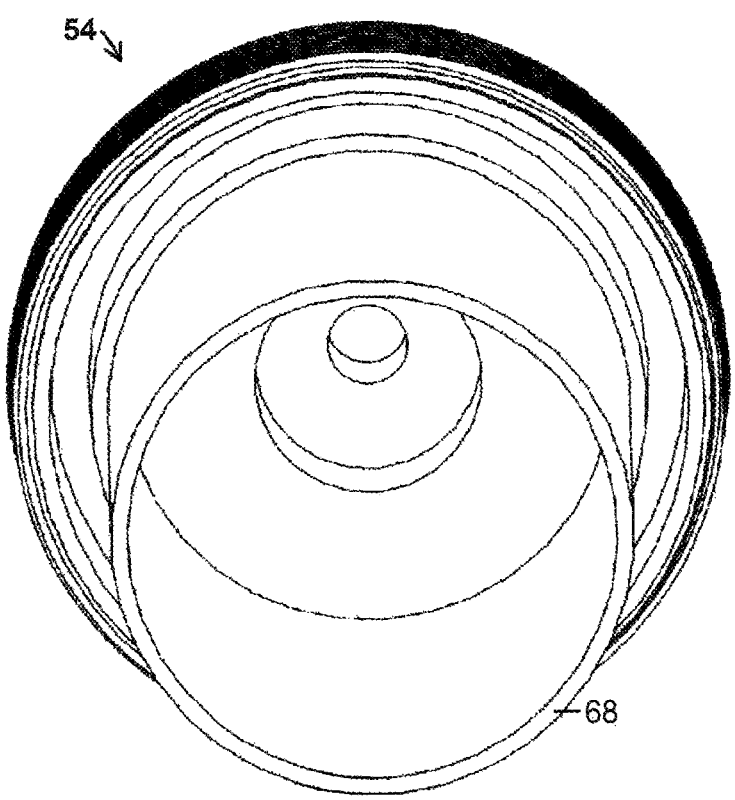
FIG. 18 is a tilted back view of the removable hose inlet of the Germicidal UV Light Device.
Figure 19:
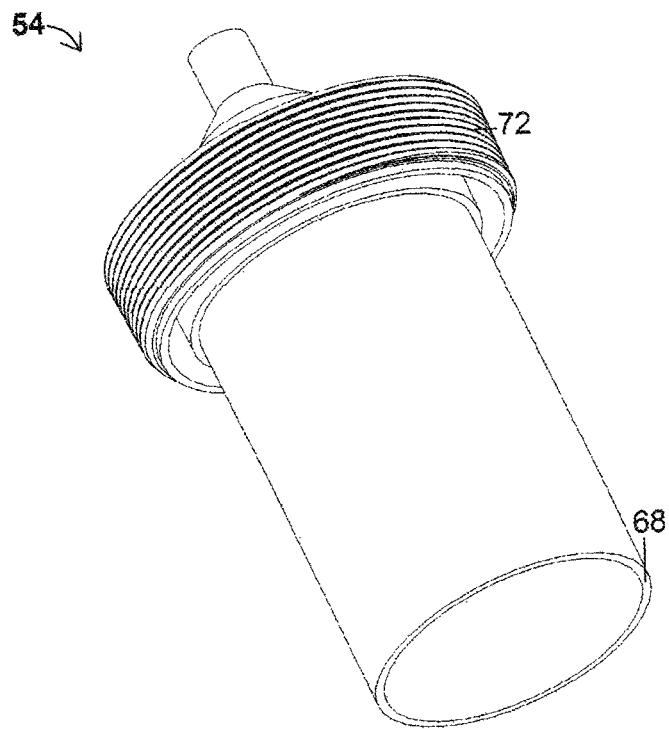
FIG. 19 is a tilted forward view of the removable hose inlet of the Germicidal UV Light Device.
Figure 20:
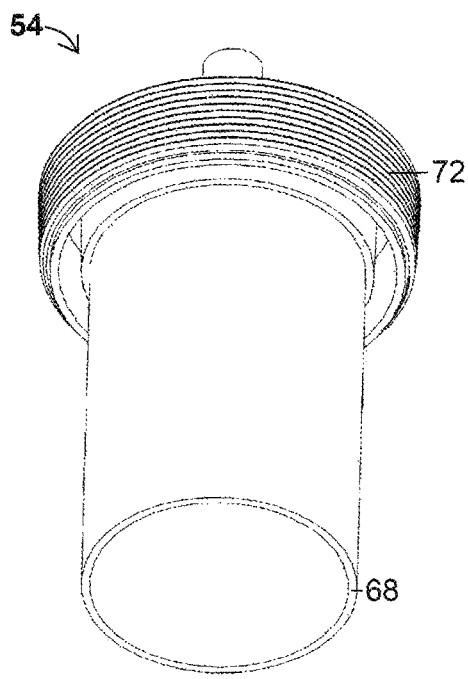
FIG. 20 is a tilted forward view of the removable hose inlet of the Germicidal UV Light Device.
Figure 21:
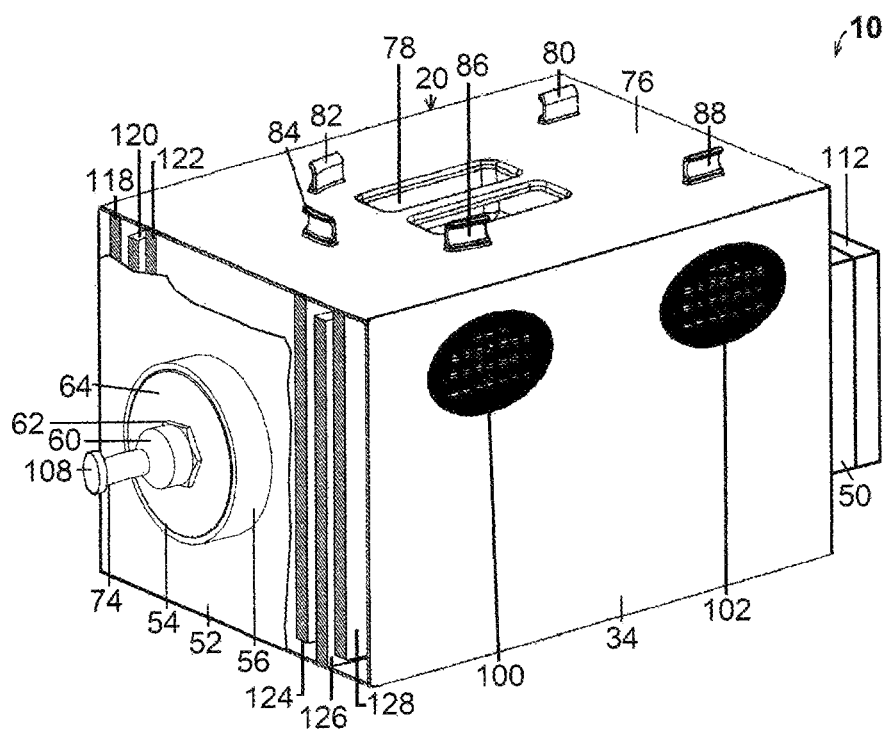
FIG. 21 is a tilted cut away view with cap of the Germicidal UV Light Device.
Figure 22:
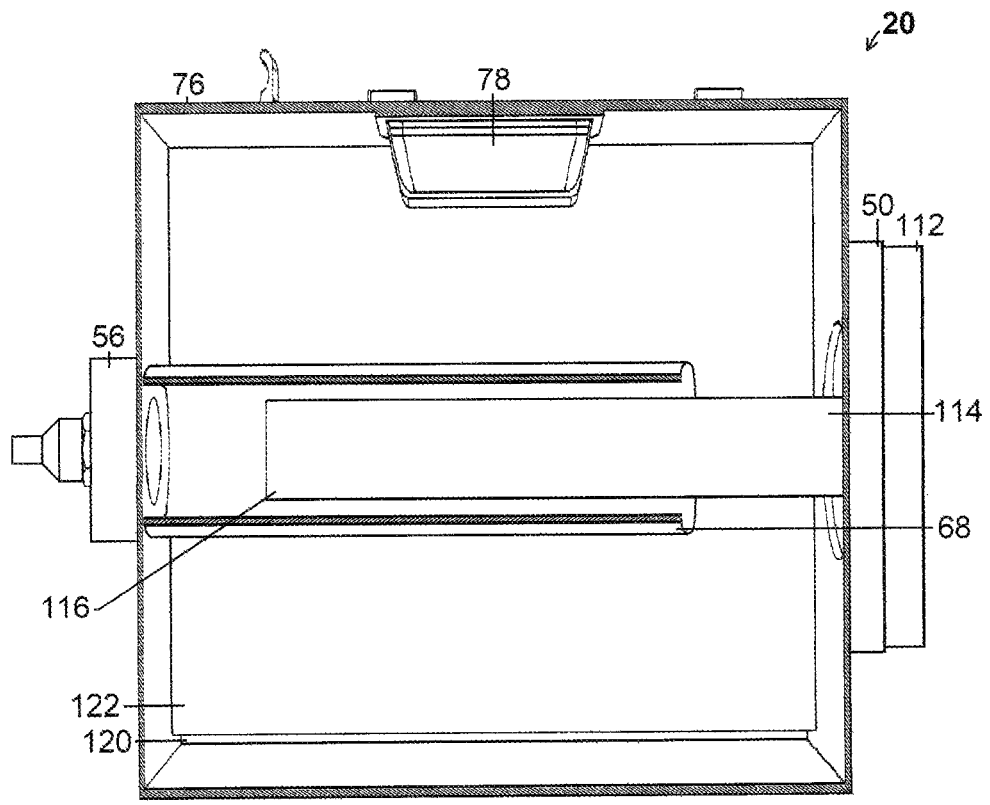
FIG. 22 is a front view cut away of vented container of the Germicidal UV Light Device.
Figure 23:
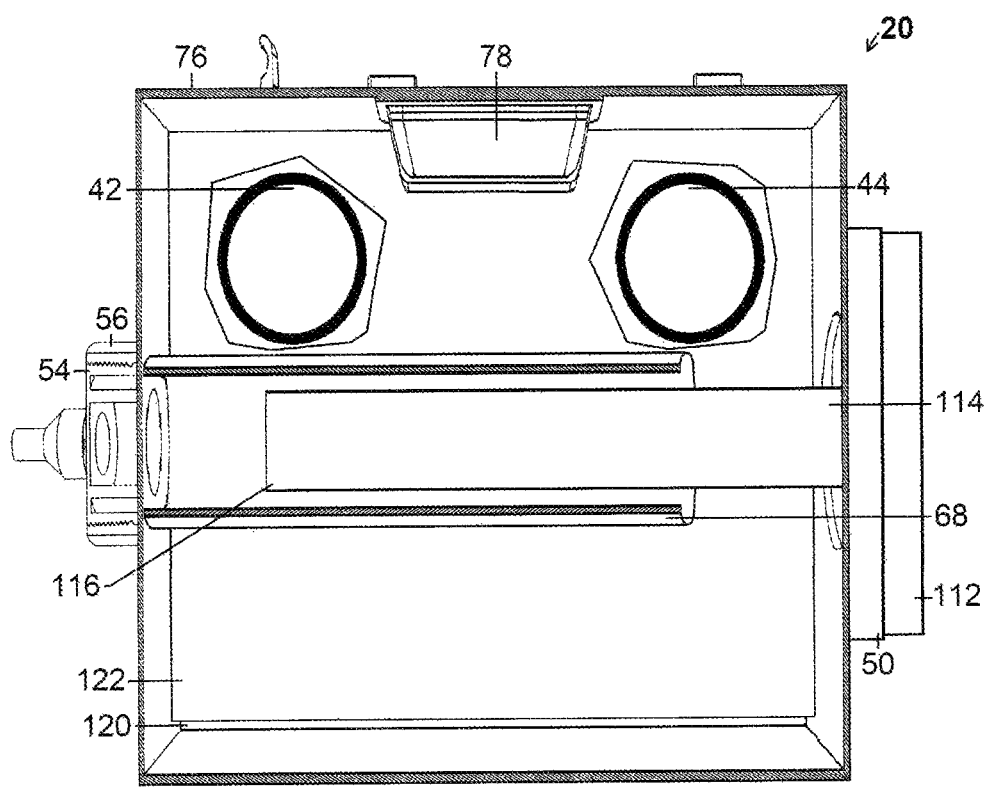
FIG. 23 is a front view cut away with baffle cut away of vented container of the Germicidal UV Light Device.
Figure 24:
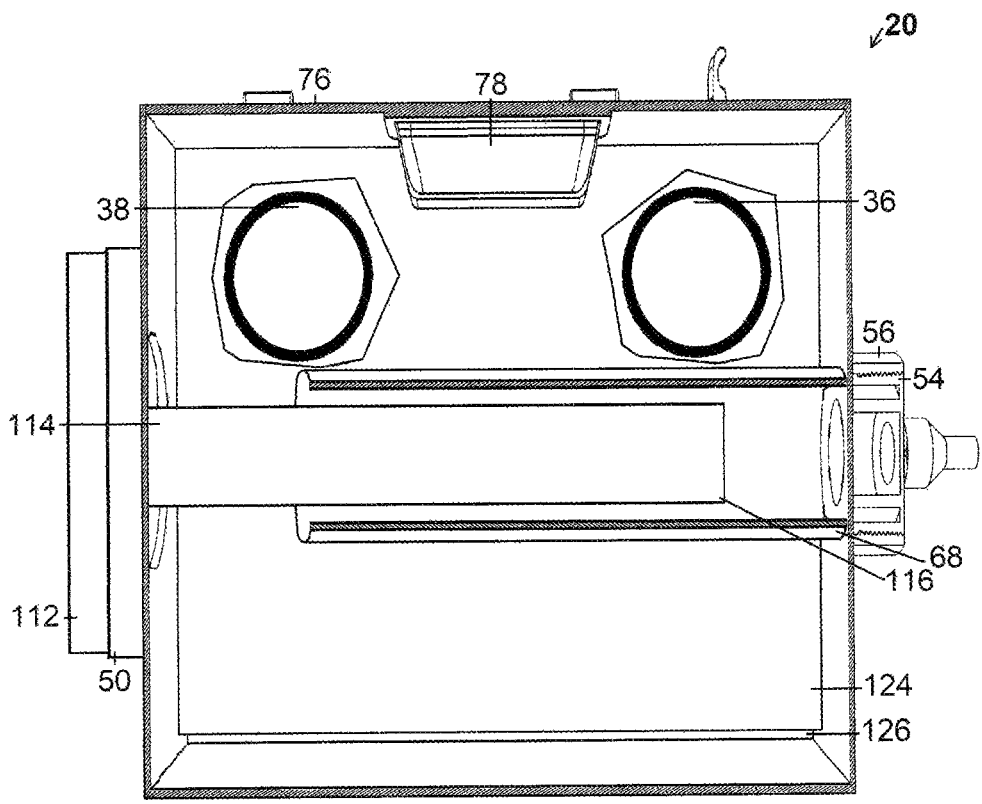
FIG. 24 is a back view cut away with baffle cut away of vented container of the Germicidal UV Light Device.

Said vented container 20 further comprises a front wall 34, as shown in FIGS. 1, 2, 3, 4, and 21 having an opening 36 and 38, as shown in FIGS. 2, 4 and 24; a rear wall 40, as shown in FIGS. 5 and 6 having an opening 42 and 44, as shown in FIGS. 6 and 23; a right outside wall 46, as shown in FIGS. 7 and 8 having an opening 48, as shown in FIGS. 8 and 11, and a partial encasement 50, as shown in FIGS. 1, 2, 3, 4, 5, 6, 7, 8, 12, 13, 21, 22, 23 and 24; a left outside wall 52, as shown in FIGS. 1, 2, 9, 10 and 21; a removable hose inlet 54, as shown in FIGS. 1, 9, 15, 16, 17, 18, 19, 20, 21, 23, and 24; a rim 56, shown in FIGS. 1, 2, 3, 4, 5, 6, 9, 10, 12, 13, 21, 22, 23 and 24; and a circular passageway 58 strategically positioned on said left outside wall 52, as shown in FIGS. 2 and 10. The center-point of said rim 56 and the center point of said circular passageway 58 are in direct alignment with each other. Said removable hose inlet 54 includes a tube connector 60 having a 6-sided hex nut 62 at the base of said tube connector 60 that is affixed directly with the flat base 64 of said removable hose inlet 54, as shown in FIGS. 1, 9, 15, 16 and 21. Said removable hose inlet 54 further includes a short open ended tubular shaped containment shield 68, as shown in FIGS. 15, 17, 18, 19, 20, 22, 23 and 24; an inner spiral ridges 70, as shown in FIG. 2; said rim 56 further includes outer spiral ridges 72, as shown in FIGS. 15, 19 and 20; a hose inlet end 74 which is affixed to said second end 28 of said first removable right-angle connector 16, as shown in FIGS. 1 and 21. Said inner spiral ridges 70 of said rim 56 and said outer spiral ridges 72 of said removable hose inlet 54 are matched so that said removable hose inlet 54 and said rim 56 can quickly be assembled and disassembled as desired.

Figure 13:
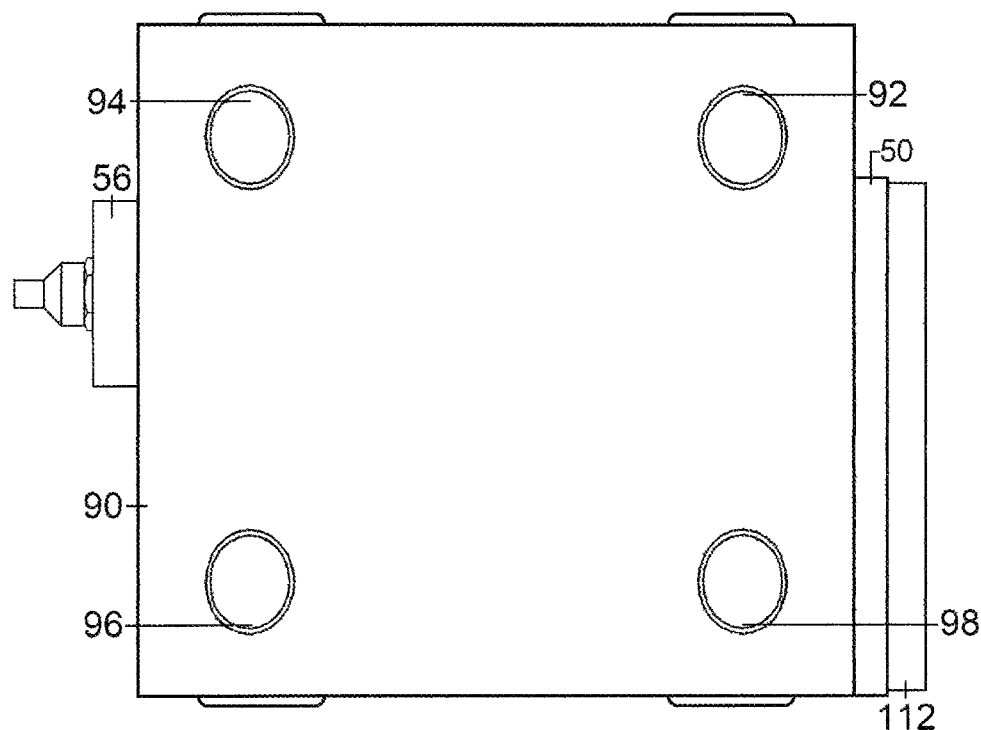
FIG. 13 is a bottom view of the Germicidal UV Light Device.

Said vented container 20 still further comprises a top 76 having a recessed handle 78, as shown in FIGS. 1, 2, 12, 21, 22, 23 and 24; a first cable holder 80; a second cable holder 82; a third cable holder 84; a fourth cable holder 86; and a fifth cable holder 88, as shown in FIGS. 1, 2, 12 and 21; a bottom 90 having an anti-skid rubber pad 92, 94, 96 and 98, as shown in FIG. 13; a screened vent 100 and 102, as shown in FIGS. 1, 3 and 21 which are affixed into said openings 36 and 38, respectively; a screened vent 104 and 106, as shown in FIG. 5 which are affixed into said openings 42 and 44, respectively; and a cap 108 designed to securely fasten to said hose inlet end 74, as shown in FIG. 21. Said cap 108 is removed from said hose inlet end 74 of said removable hose inlet 54 just prior to said second end 28 of said first removable right-angle connector 16 being affixed to said hose inlet end 74; and first end 26 of said first removable right-angle connector 16 being affixed to second end 32 of said second removable right-angle connector 18; and first end 30 of said second removable right-angle connector 18 being affixed to second connector 24 of said flexible hose 14;

and first connector 22 of said flexible hose 14 being affixed to said face mask 12. After a treatment with the Germicidal UV Light Device 10 is administered said second end 28 of said first removable right-angle connector 16 is immediately separated from said hose inlet end 74 of said removable hose inlet 54 and said cap 108 is affixed to said hose inlet end 74 of said removable hose inlet 54.

Figure 14:
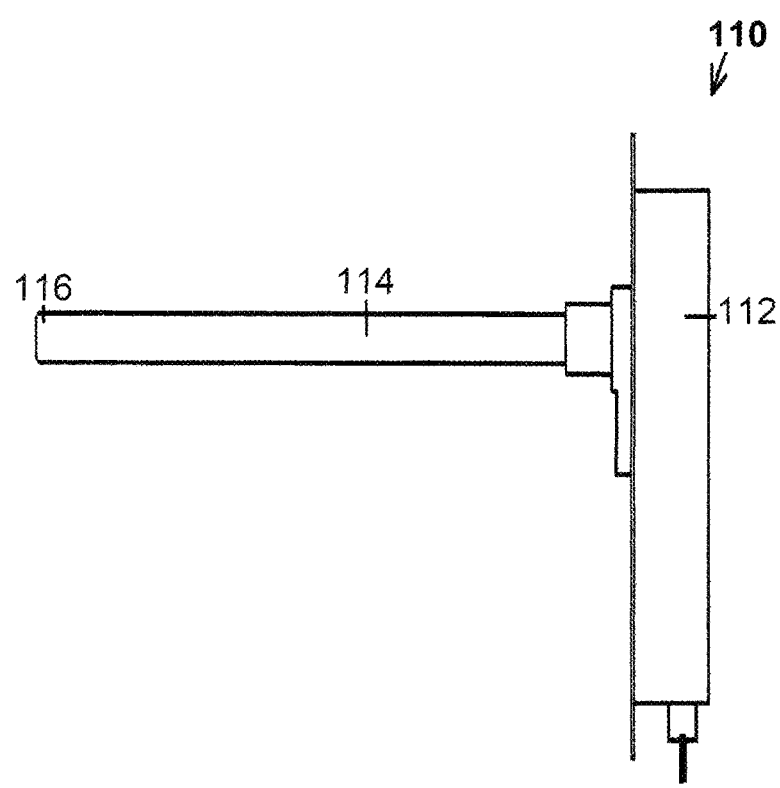
FIG. 14 is a left side view of the Evergreen UV Lumalier ADPL-135 of the Germicidal UV Light Device.

Said vented container 20 further comprises an Evergreen UV Lumalier ADPL-135 110 having a base 112, a 9" 35 W TUV Lamp 114 and a tip 116, as shown in FIG. 14. The base 112 of said Evergreen UV Lumalier ADPL-135 110 carries said 9" 35 W TUV Lamp 114, as shown in FIG. 14 and is seated within said partial encasement 50 of said right outside wall 46 of said vented container 20, as shown in FIG. 7. Once said 9" 35 W TUV Lamp 114 is fully inserted, the base 112 is secured within said partial encasement 50 of said right outside wall 46 of said vented container 20 wherein the center-point of said tip 116 of said 9" 35 W TUV Lamp 114 and the center point of said hose inlet end 74 are in direct alignment and close proximity with each other, as shown in FIGS. 22, 23 and 24.

Said vented container 20 even further includes a UV light baffle 118, 120, 122, 124, 126 and 128, as shown in FIGS. 1, 11, 21, 22, 23 and 24. Said UV light baffle's are purposefully designed and strategically placed to fully eliminate the possibility of anyone viewing direct and/or a reflected light from said 9" 35 W TUV Lamp 114 at any time, while allowing the necessary airflow into and out of said vented container 20, as shown in FIG. 1.

Said Germicidal UV Light Device 10 does utilize said Evergreen UV Lumalier ADPL-135 110 having said base 112 and said 9" 35 W TUV Lamp 114. Said 9" 35 W TUV Lamp 114, also known as the "UV Germicidal Ultraviolet Lamp", and/or, the UV-C, and/or, the "germicidal ultraviolet", having a specific wavelength of 253.7 nanometers (253.7 billionths of a meter) known to deactivate molds, spores and germs contained in tiny airborne droplet nuclei that transmit diseases such as measles, tuberculosis, and influenza from person to person is the only suitable UV-C germicidal ultraviolet, at this time, that will be used in the Germicidal UV Light Device 10. With significant penetrating ability, UV-C can penetrate the cell wall of a microorganism and destroy it, but it cannot penetrate the outer layer of human skin or the cornea of the eye, although overexposure may lead to a temporary, minor eye irritation or skin reddening, it does not cause serious or long-term health effects. In addition, the UV-C germicidal ultraviolet having a specific wavelength of 253.7 nanometers will destroy ozone. There is in the making Far-UVC light, which is a narrow spectrum within UV-C light, provides the same effect of killing pathogens as UV-C light. However, Far-UVC lamps have not yet been approved by the US Food and Drug Administration. If the Far-UVC lamps are approved, then they would be suitable for use in said Germicidal UV Light Device 10.

When in operation, during a treatment session, said Germicidal UV Light Device 10 momentarily captures the exhaled breath of a SARS-CoV-2 patient within a said open ended tubular shaped containment shield 68 of said removable hose inlet 54 where the already activated Evergreen UV Lumalier ADPL-135 110 9" 35 W TUV Lamp 114 having a specific wavelength of 253.7 nanometers (253.7 billionths of a meter) immediately inactivates all of the live active SARS-CoV-2 virions contained within the exhaled breath, thereby creating at least one (literally thousands per studies made) UV-C inactivated SARS-CoV-2 whole virus particles/virions; and then, with the next inhaled breath of said SARS-CoV-2 patient at least one (literally thousands per studies made) of said UV-C inactivated SARS-CoV-2 whole and/or partial particle(s) are carried into the respiratory tract of said SARS-CoV-2 patient. Eventually, at least one UV-C inactivated SARS-CoV-2 whole and/or partial particle(s) is captured by the dendritic cell(s) marking the very beginning of antibody creation. Said Germicidal UV Light Device 10 also provides a method to harvest the remaining said UV-C inactivated SARS-CoV-2 whole and/or partial particles within said Germicidal UV Light Device 10 for immediate vaccine purposes of front line workers. Said UV-C inactivated SARS-CoV-2 whole and/or partial particles that remained within said short open ended tubular shaped containment shield 68 are collected for purposes of vaccine administration by mouth, and/or, by injection, and/or, by a nebulizer.

Said Germicidal UV Light Device 10 is not limited to treatment of patients having the SARS-CoV-2 virus but may be used to inactivate other viruses and/or bacteria's and in some instances may produce an effective and appropriate vaccine. In general, treatment with the Germicidal UV Light Device is a very safe, low-risk beneficial addition to the plan of care for any SARS-CoV-2 patient in the early stages of the infection providing that all instructions and precautions are followed.

Figure 25:
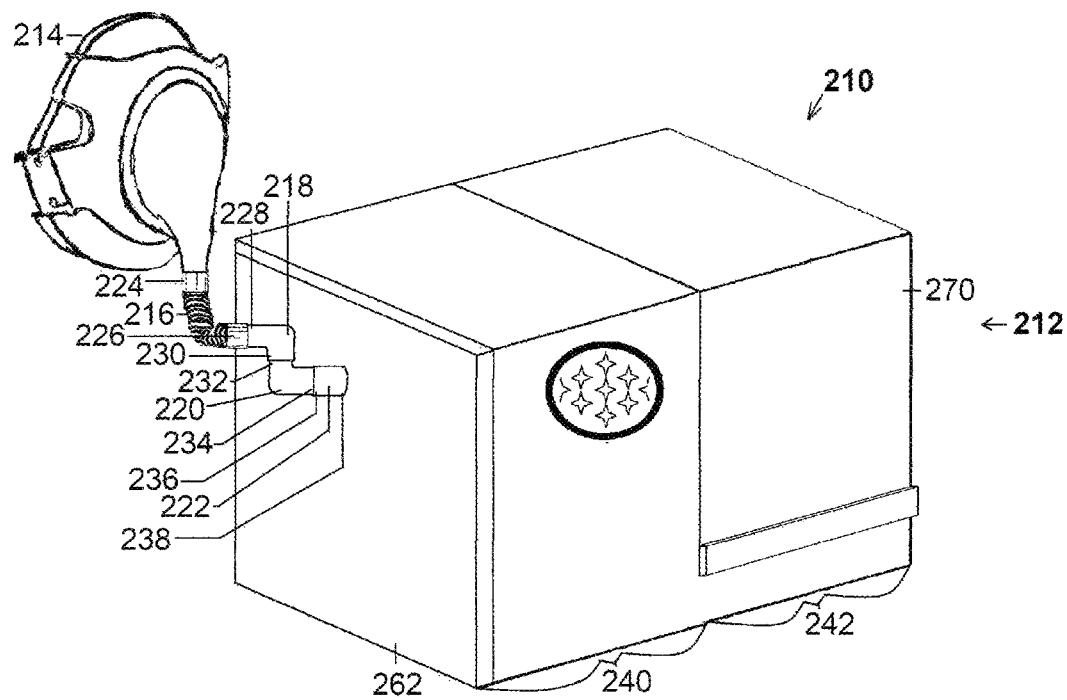
FIG. 25 is a tilted view of another embodiment of the Germicidal UV Light Device.

In another Preferred Embodiment, the Germicidal UV Light Device 210 comprises a compartmental container 212; a mask 214; a flexible hose 216; a first right-angle connector 218; a second right-angle connector 220; and a straight connector 222, as shown in FIG. 25. Said mask 214 fully covers the mouth and both of the nostril areas having an unrestricted bidirectional air passageway. Said flexible hose 216 includes a first connector 224 and a second connector 226, as shown in FIG. 25. Said first right-angle connector 218 includes first end 228 and second end 230, as shown in FIG. 25. Said second right-angle connector 220 includes first end 232 and second end 234. Said straight connector 222 includes first end 236 and second end 238, as shown in FIG. 25.

Figure 26:
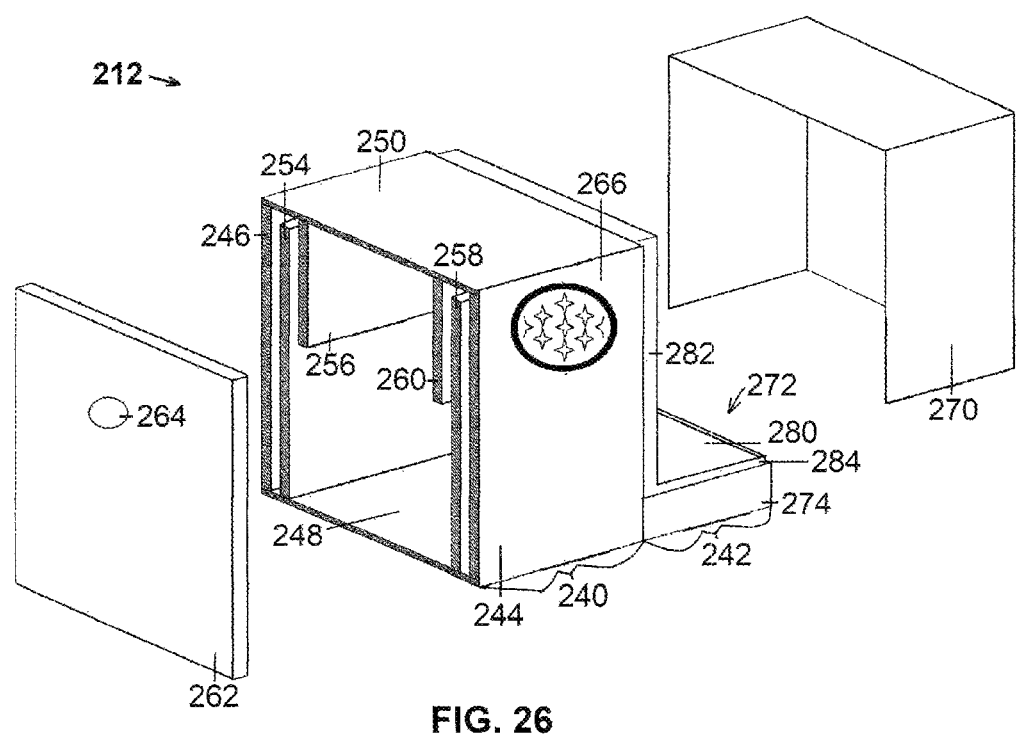
FIG. 26 is exploited sectional tilted view of the Germicidal UV Light Device.
Figure 27:
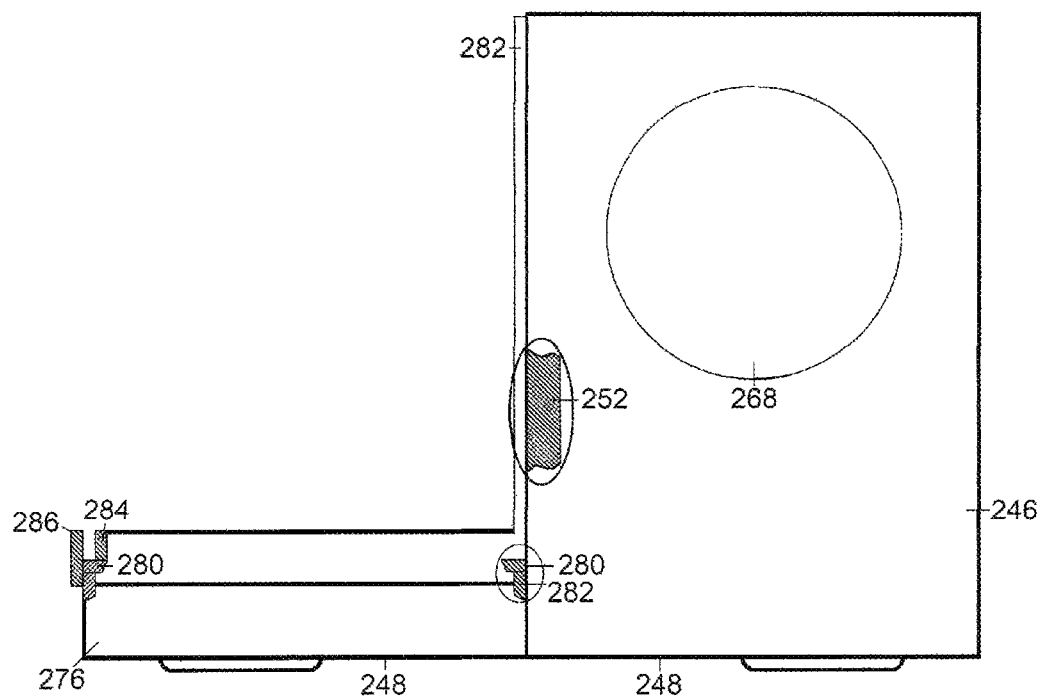
FIG. 27 is a left side partial cut away view of the Germicidal UV Light Device.
Figure 28:
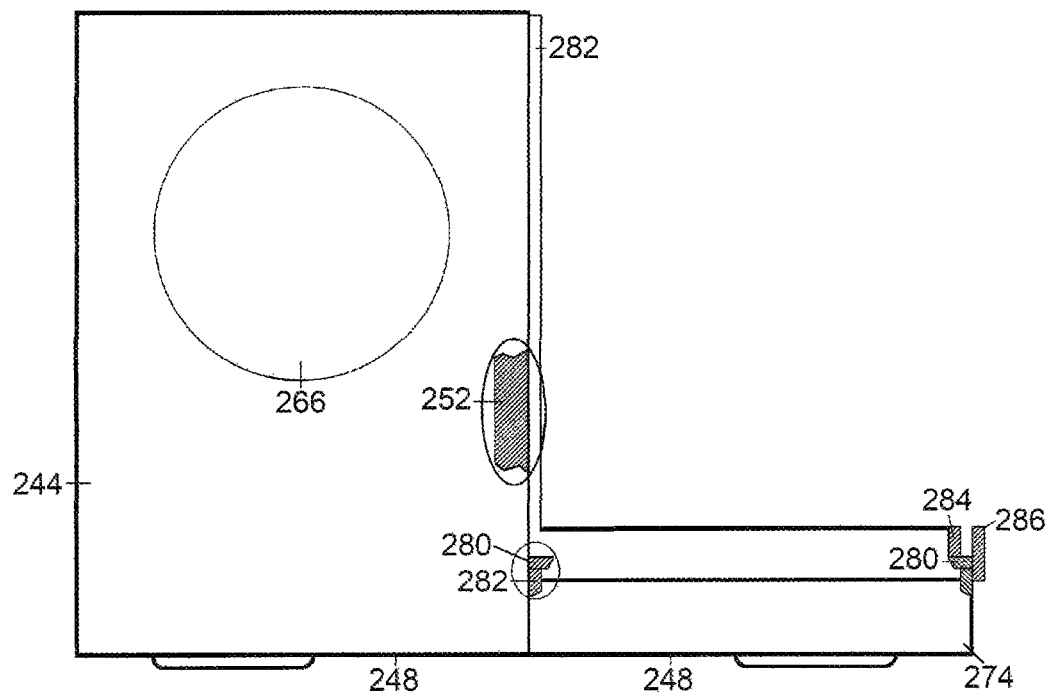
FIG. 28 is a right side partial cut away view of the Germicidal UV Light Device.
Figure 29:
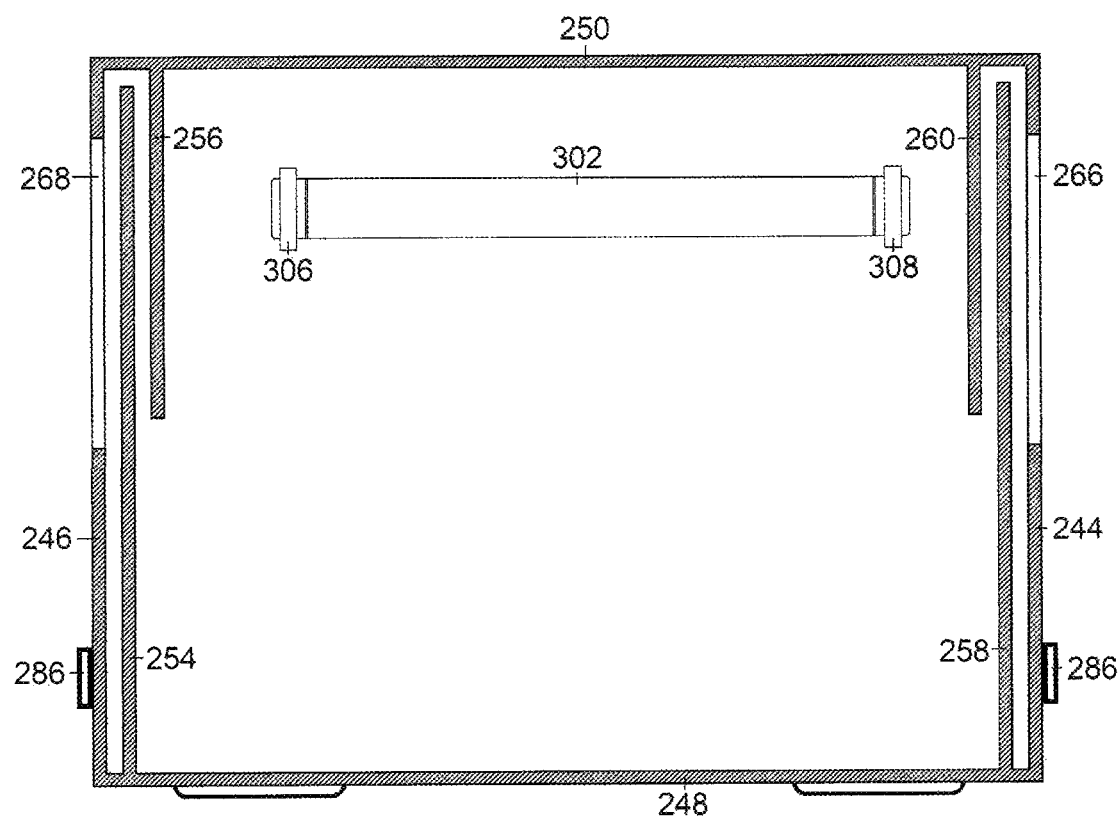
FIG. 29 is a cut away view of the accessible compartment of the Germicidal UV Light Device.

Said compartmental container 212 includes a front compartment 240, and a back compartment 242, as shown in FIGS. 25 and 26. Said front compartment 240 includes a right side wall 244, as shown in FIGS. 26, 28 and 29; a left side wall 246, as shown in FIGS. 26, 27 and 29; a shared bottom 248, as shown in FIGS. 26, 29, 30 and 32; a top 250, as shown in FIGS. 26 and 29; a shared back wall 252, as shown in FIGS. 27 and 28; an outer left side baffle 254, as shown in FIGS. 26 and 29; an inner left side baffle 256, as shown in FIGS. 26 and 29; an outer right side baffle 258, as shown in FIGS. 26 and 29; an inner right side baffle 260, as shown in FIGS. 26 and 29; and a removeable flat door 262 having 22 mm hole 264 whose center is approximately 6¾"×1⅜" as shown in FIGS. 25 and 26. In addition, said front compartment 240 further includes a first 2.9375" screened hole 266, as shown in FIGS. 26, 28 and 29 and a second 2.9375" screened hole 268, as shown in FIGS. 27 and 29.

Figure 30:
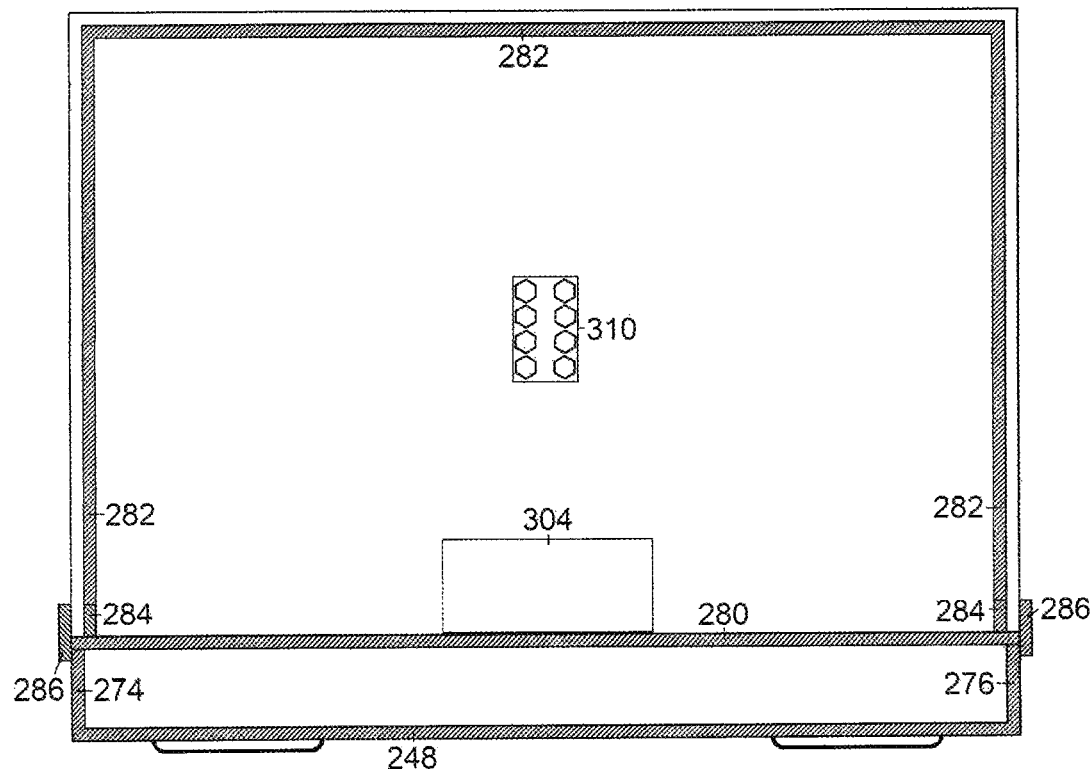
FIG. 30 is a cut away view of the inaccessible compartment of the Germicidal UV Light Device.
Figure 31:
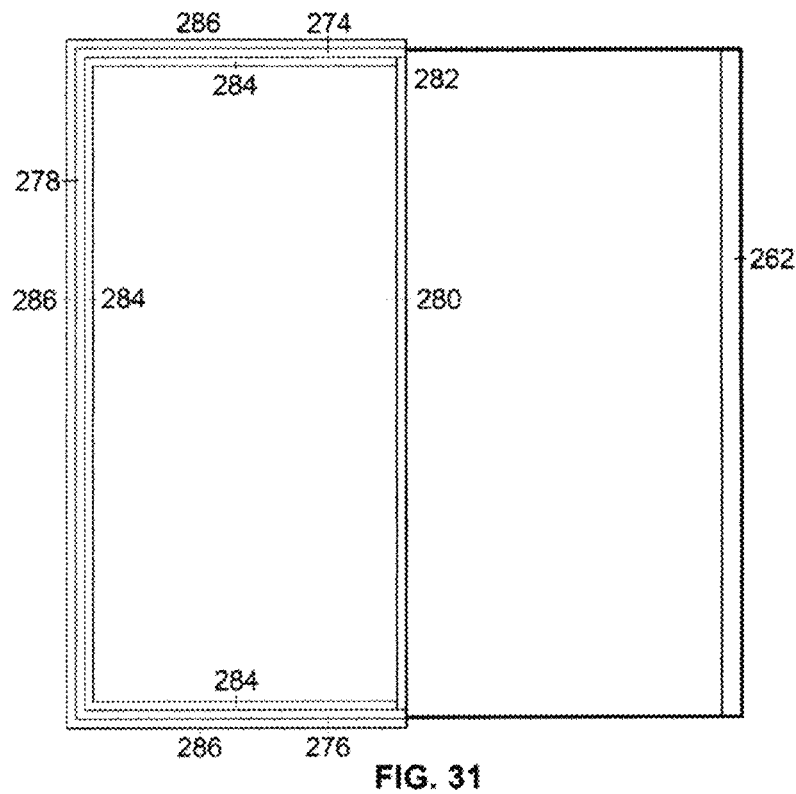
FIG. 31 is a top view partial cut away of the Germicidal UV Light Device.
Figure 32:
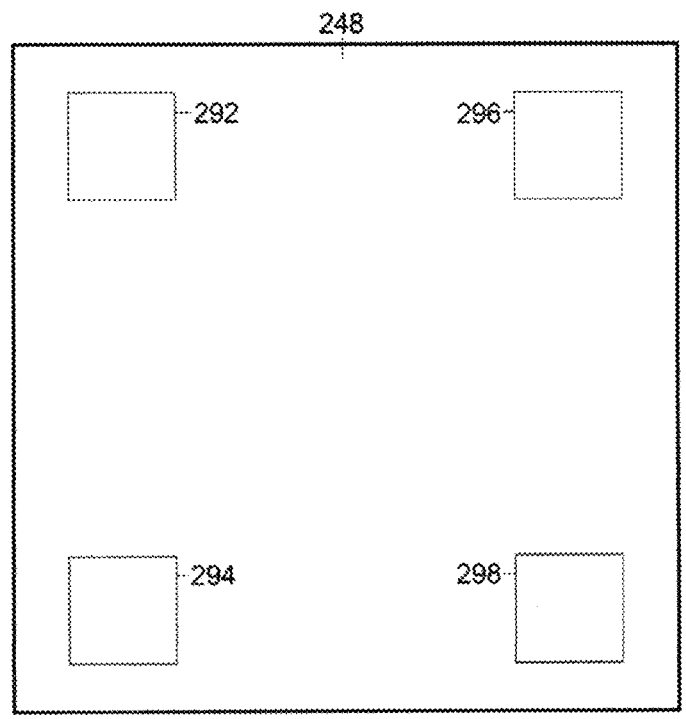
FIG. 32 is a bottom view of the Germicidal UV Light Device.
Figure 33:
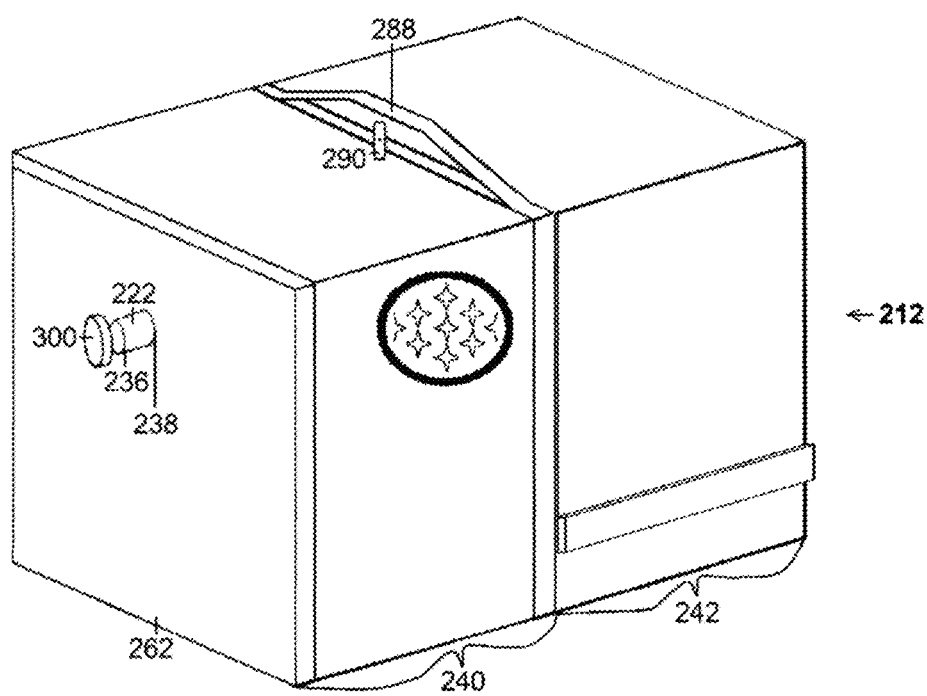
FIG. 33 a tilted assembled view with cap of the Germicidal UV Light Device.

Said back compartment 242 includes a cover 270, as shown in FIGS. 25 and 26 a base 272, as shown in FIG. 26; having a said shared bottom 248, as shown in FIGS. 26, 27, 28, and 30; a right-side 274 extended from the lower portion of said right side wall 244, as shown in FIGS. 26, 28, 30 and 31; a left-side 276 extended from the lower portion said left-side wall 246, as shown in FIGS. 27, 30 and 31; a back wall 278, as shown in FIG. 31; a false bottom 280, as shown in FIGS. 26, 27, 28, 30 and 31; a first partial inner boundary support ridge 282 for said cover 270 is affixed to said shared back wall 252, as shown in FIGS. 26,27, 28, 30 and 31; a second inner boundary support ridge 284 for said cover 270, as shown in FIGS. 26, 27, 28, 30 and 31; an outer boundary support ridge 286 for said cover 270, as shown in FIGS. 27, 28, 29, 30 and 31; and a handle 288 having a swivel latch 290, as shown in FIG. 33. Said shared bottom 248 includes a first platform 292, a second platform 294, a third platform 296 and a fourth platform 298, as shown in FIG. 32, for the attachment of anti-skid rubber pads, not shown.

Said second end 238 of said straight connector 222 is firmly inserted into said hole 264 (see FIG. 26 hole 264 only) of said removeable flat door 262, as shown in FIGS. 25 and 33. Said second end 234 of said second right-angle connector 220 is connected to said first end 236 of said straight connector 222, as shown in FIG. 25. Said second end 230 of said first right-angle connector 218 is connected to said first end 232 of said second right-angle connector 220, as showing FIG. 25. Said first end 228 of said first right-angle connector 218 is connected to said second connector 226 of said flexible hose 216, as shown in FIG. 25. Said first connector 224 of said flexible hose 216 is connected to said mask 214, as shown in FIG. 25.

Said Germicidal UV Light Device 210 still further comprises cap 300 designed to securely fasten to said first end 236 of said straight connector 222, as shown in FIG. 33; a far-UVC lamp 302, such as a 40-Watt Far UV 222 nm Shatterproof Lamp, 8" Bulb, 6500uW Output Far UV-C, as shown in FIG. 29; a ballast 304 such as a 120V Ballast to power said UV lamp 302, as shown in FIG. 30; a first mounting bracket 306; a second mounting bracket 308, as shown in FIG. 29; and block terminal 310, such as a Dual Rows 4 Positions 600V 45A Cable Barrier Block Terminal Strip TB-4504L, as shown in FIG. 30.

Said far-UVC lamp 302 and said ballast 304 are electrically connected and can be purchased in a kit such as the 40-Watt Far UV 222 nm Shatterproof Lamp Kit, 8" Bulb, 6500 uW Output Far UVC, Lamp w/Ballast, Skin Safe FRL-EMY-8-40 W-FUVC-KT-120V-SPF.

Said hole 264 is in close proximity with said far-UVC lamp 302 so that the air entering said front compartment 240 of said compartmental container 212 via said hole 264 would circulate around said far-UVC lamp 302. In addition, any air drawn from said front compartment 240 of said compartmental container 212 via said hole 264 would have been exposed to said far-UVC lamp 302 just prior to exiting said compartmental container 212.

Said outer left side baffle 254, said inner left side baffle 256, said outer right side baffle 258 and said inner right side baffle 260 are purposefully designed and strategically placed to fully eliminate the possibility of anyone viewing any of the light from said far-UVC lamp 302 when in operation, even though the 40-Watt Far UV 222 nm Shatterproof UV Lamp 302 is said to be safe enough. So, the light if viewed would cause no damage to the eye or skin. This added precautionary measure increases the safe use of said Germicidal UV Light Device 210.

Said Germicidal UV Light Device 210 does utilize said 40-Watt Far UV 222 nm Shatterproof far-UVC lamp 302 to penetrate the cell wall of a microorganism and destroy it, but it cannot penetrate the outer layer of human skin or the cornea of the eye. Therefore, there is not any known health issues.

When in operation, during a treatment session, said Germicidal UV Light Device 210 momentarily captures the exhaled breath of a SARS-CoV-2 patient within said front compartment 240 of said compartmental container 212 where the already activated 40-Watt Far UV 222 nm Shatterproof far-UVC lamp 302 immediately inactivates all of the live active SARS-CoV-2 virions contained within the exhaled breath, thereby creating at least one (literally thousands per studies made) far-UVC inactivated SARS-CoV-2 whole virus particles/virions; and then, with the next inhaled breath of said SARS-CoV-2 patient literally thousands of far-UVC inactivated SARS-CoV-2 whole and/or partial particle(s) are carried into the respiratory tract and when at least one of the far-UVC inactivated SARS-CoV-2 whole and/or partial particle(s) are captured by the dendritic cell(s) triggering the Innate and Adaptive Immune System to be activated marking the very beginning of antibody creation. Once studies have commenced and completed an accurate account of exactly what happens will be made known.

Said Germicidal UV Light Device 210 is not limited to treatment of patients having the activated SARS-CoV-2 virus but may be used to inactivate other viruses and/or bacteria's and in some instances may produce an effective and appropriate vaccine for purposes of administration by mouth, and/or, by injection, and/or, by a nebulizer. In general, treatment with the Germicidal UV Light Device can be a very safe, low-risk beneficial addition to the plan of care for a SARS-CoV-2 patient providing all instructions, precautions and appropriate methods are followed.

Figure 34:
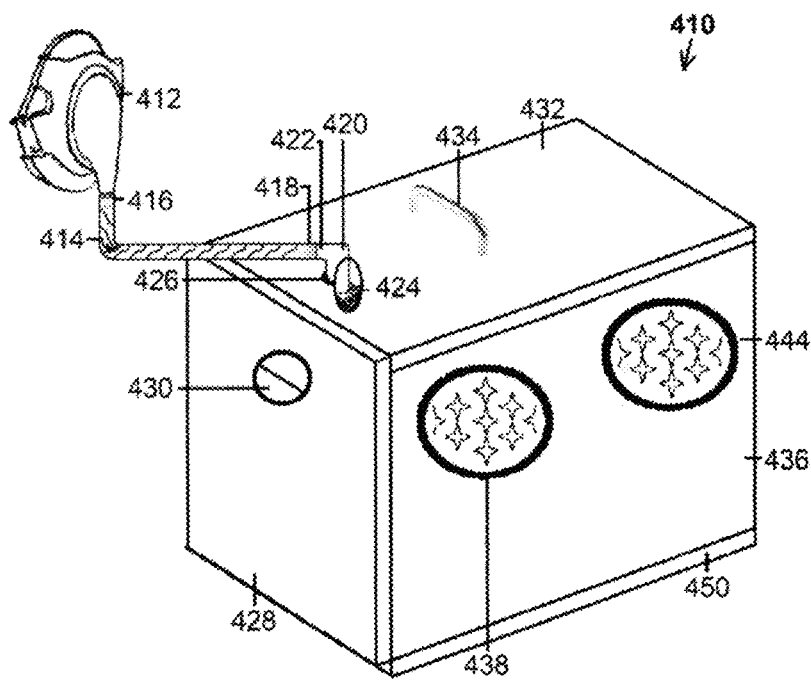
FIG. 34 is an assembled slanted view of the Germicidal UV Light Device.
Figure 35:
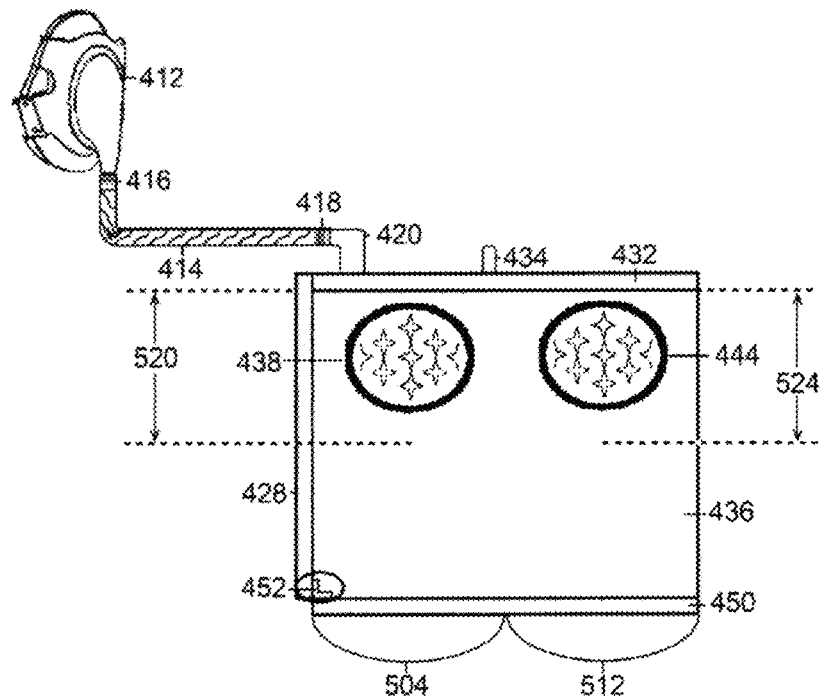
FIG. 35 is a right side view of the Germicidal UV Light Device.
Figure 36:
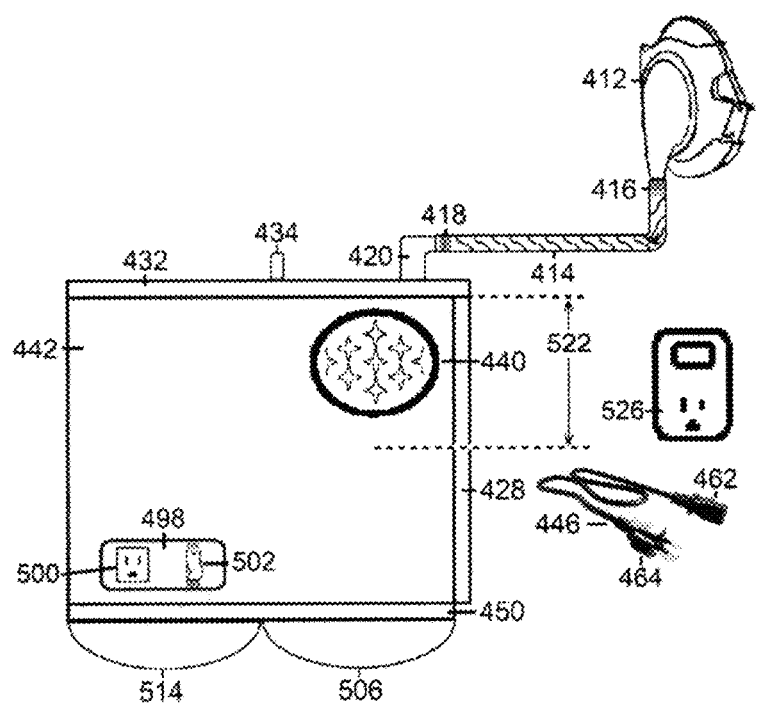
FIG. 36 is a left side view of the Germicidal UV Light Device.
Figure 37:
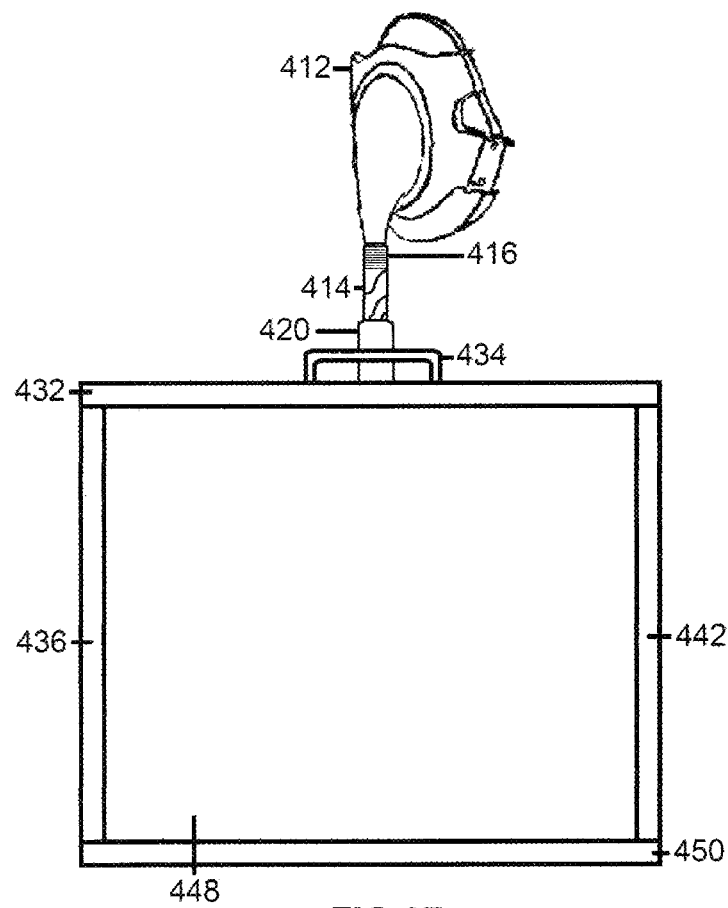
FIG. 37 is a back view of the Germicidal UV Light Device.
Figure 38:
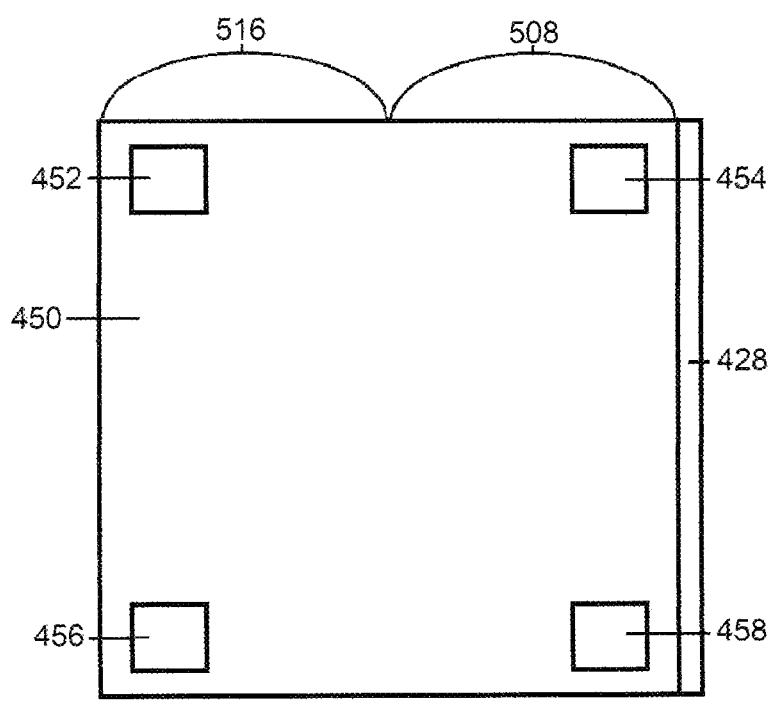
FIG. 38 is a bottom view of the Germicidal UV Light Device.
Figure 39:
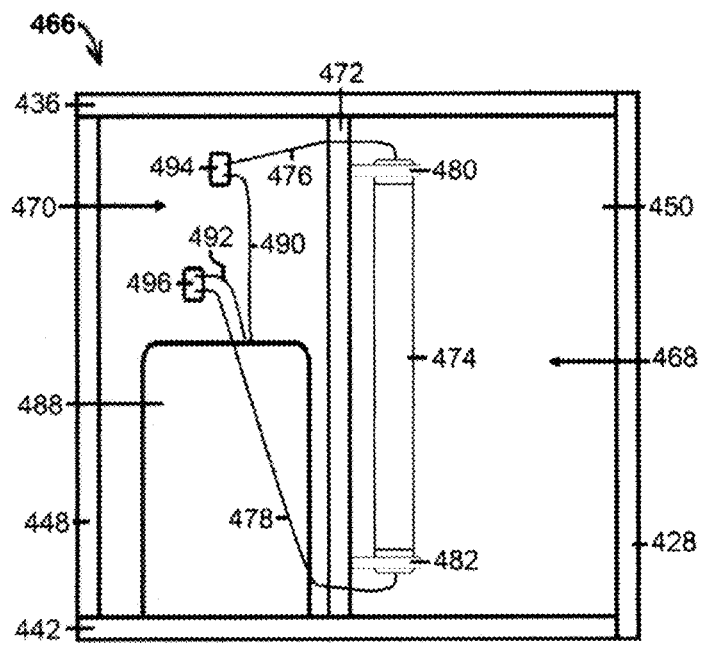
FIG. 39 is a cut-away downward view of the accessible compartment and inaccessible compartment of the compartmental container of the Germicidal UV Light Device.
Figure 40:
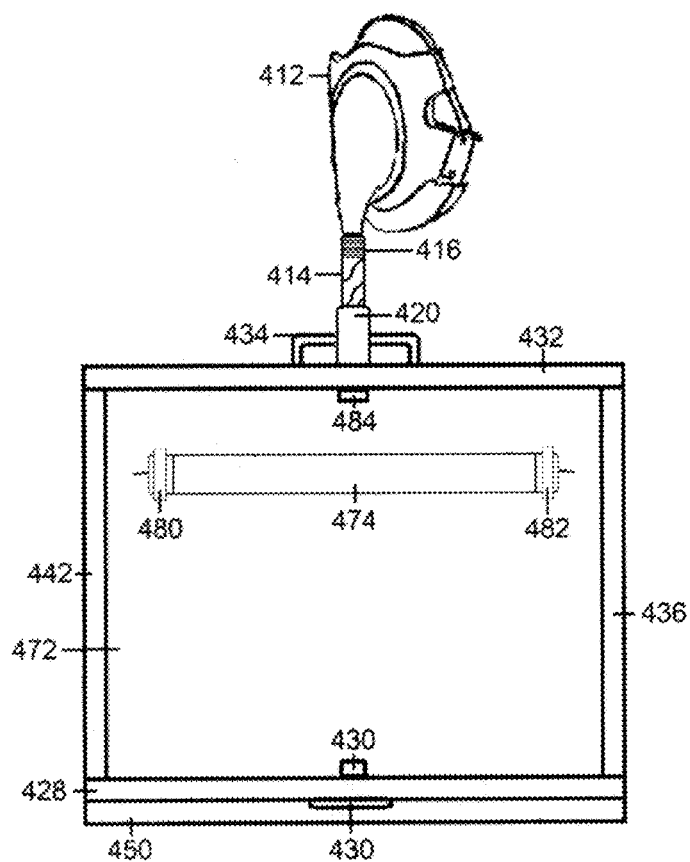
FIG. 40 is an inside view of the accessible compartment of the Germicidal UV Light Device.
Figure 41:
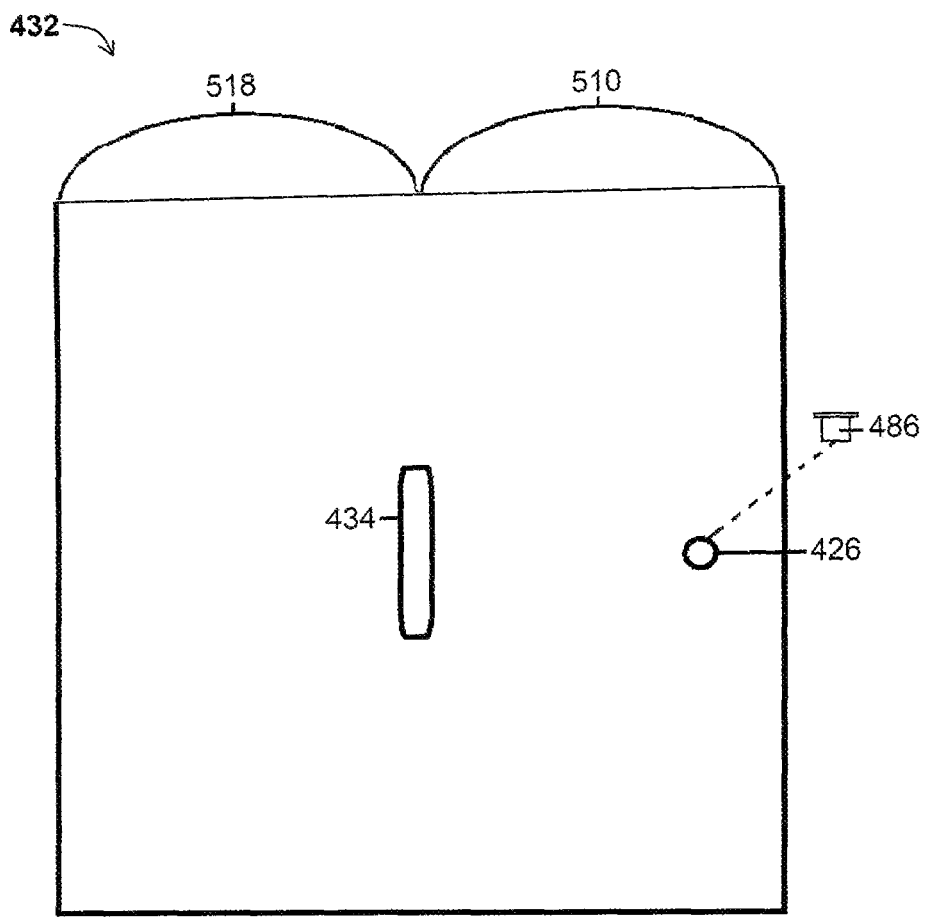
FIG. 41 is a downward view of the top of the Germicidal UV Light Device.
Figure 42:
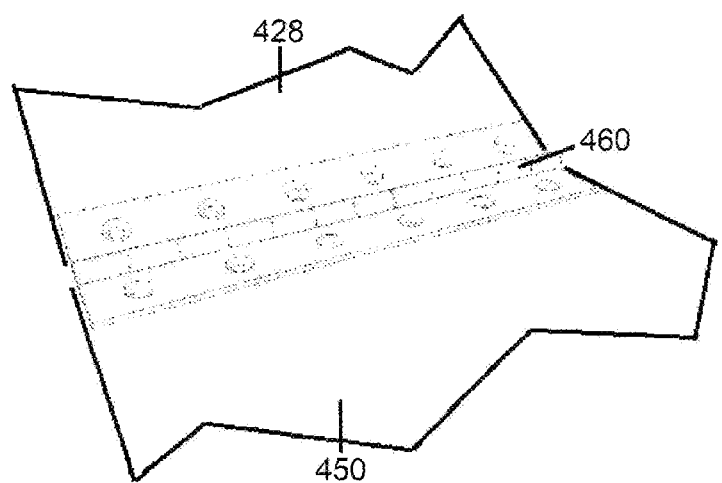
FIG. 42 is a cut-away partial view of the door hinged to the bottom of the Germicidal UV Light Device.

In yet another Preferred Embodiment, the Germicidal UV Light Device 410 comprises a mask 412, as shown in FIGS. 34, 35, 36, 37 and 40; a flexible hose 414, as shown in FIGS. 34, 35, 36, 37 and 40; a first connector 416 as shown in FIGS. 34, 35, 36, 37 and 40; and a second connector 418, as shown in FIGS. 34 and 35; a right-angle connector 420, as shown in FIGS. 34, 35, 36, 37 and 40 having a first end 422, as shown in FIG. 34, and second end 424, as shown in FIG. 34; an opening 426, as shown in FIGS. 34 and 41; a door 428, as shown in FIGS. 34, 35, 36, 38, 39 and 42, having a key locking latch 430, as shown in FIGS. 34 and 40, such as the Stellar Series Stainless Steel Flush Latch; a top 432, as shown in FIGS. 34, 35, 36, 37, 40 and 41, and a handle 434, as shown in FIGS. 34, 35, 36, 37, 40 and 41; a right-side wall 436, as shown in FIGS. 34, 35, 37 and 40; a first round screen vent 438, as shown in FIGS. 34 and 35; a second round screen vent 440, as shown in FIGS. 34 and 35; a left-side wall 442, as shown in FIGS. 36, 37, 39 and 40; a third round screen vent 444, as shown in FIG. 36; and an detachable AC power cord 446, as shown in FIG. 36; a back wall 448, as shown in FIGS. 37 and 39; a bottom 450, as shown in FIGS. 34, 35, 36, 37, 38, 39, 40 and 42; a first self-adhesive anti-skid rubber pad 452; as shown in FIG. 38; a second self-adhesive anti-skid rubber pad 454; as shown in FIG. 38; a third self-adhesive anti-skid rubber pad 456; as shown in FIG. 38; a fourth self-adhesive anti-skid rubber pad 458, as shown in FIG. 38; a continuous hinge 460, as shown in FIGS. 35 and 42; and a countdown auto shut-off safety outlet 526, as shown in FIG. 36. Said detachable AC power cord 446, as shown in FIG. 36 comprises a three-prong receptacle 462 as shown in FIG. 36; and a plug 464, as shown in FIG. 36. Said countdown auto shut-off safety outlet 526, such as the SIMPLE TOUCH Auto Shut-Off Safety Outlet plugs into a common 120 V wall outlet. Said plug 464 of said detachable AC power cord 446 plugs into said countdown auto shut-off safety outlet 526. In operation the timer is set to the desired minutes of operation in five minute increments. Seconds prior to a qualified trained Medical Professional administering any type of treatment with said Germicidal UV Light Device 410 said qualified trained Medical Professional sets the desired time on said countdown auto shut-off safety outlet 526 and the countdown commences immediately.

Said Germicidal UV Light Device 410 further comprises a compartmental container (housing) 466, as shown in FIG. 39. Said compartmental container 466 comprises a front accessible compartment 468, as shown in FIG. 39; a back inaccessible compartment 470, as shown in FIG. 39; and a common wall 472, as shown in FIGS. 39 and 40. Said front accessible compartment 468 comprises far-UVC lamp 474, such as a 40-Watt Far UV 222 nm Shatterproof Lamp, 8" Bulb, 6500 uW Output Far UV-C Far UV-C, as shown in FIGS. 39 and 40, having a connecting wire 476 and 478, as shown in FIG. 39; a first mounting bracket 480, as shown in FIGS. 39 and 40; a second mounting bracket 482, as shown in FIGS. 39 and 40; a 90° Angled Keeper 484, as shown in FIG. 40; and an insertable cap 486, as shown in FIG. 41.

Said back inaccessible compartment 470 comprises ballast 488, such as a 120V Ballast, as shown in FIG. 39 having connecting wire 490 and 492, as shown in FIG. 39; a first wire connector 494, such as the King Innovation 95015 AlumiConn Wire Connector, as shown in FIG. 39; and a second wire connector 496, such as the King Innovation 95015 AlumiConn Wire Connector, as shown in FIG. 39. Said ballast 488 of said back inaccessible compartment 470 comprises operational panel 498 whose outside surface is mounted evenly with the outside surface of said left wall 442, as shown in FIG. 36. Said operational panel 498 of said Ballast 488, as shown in FIG. 36 comprises a three prong male connector 500, as shown in FIG. 36; and an On and OFF switch 502, as shown in FIG. 36.

Said mask 412 having an unrestricted bidirectional air passageway, fully covers the mouth and both nostril areas of the person receiving treatment. Said first anti-skid rubber pad 452, said second anti-skid rubber pad 454, said third anti-skid rubber pad 456 and said fourth anti-skid rubber pad 458 are each equally spaced a certain distance and secured to said bottom 450.

Said front accessible compartment 468 includes a front portion 504 of said right-side wall 436, as shown in FIG. 35; a front portion 506 of said left-side wall 442, as shown in FIG. 36; a front portion 508 of said bottom 450, as shown in FIG. 38; and said shared common wall 472, as shown in FIG. 39; and a front portion 510 of said top 432 having a said opening 426, as shown in FIG. 41. Said back inaccessible compartment 470 includes a back portion 512 of said right-side wall 436, as shown in FIG. 35; a back portion 514 of said left-side wall 442, as shown in FIG. 36; a back portion 516 of said bottom 450, as shown in FIG. 38; and said shared common wall 472, as shown in FIG. 39; and a back portion 518 of said top 432, as shown in FIG. 41.

Said first round screen vent 438 is strategically positioned in the upper portion 520 of said front portion 504 of said right-side wall 436, as shown in FIG. 35 and said second round screen vent 440 is strategically positioned in the upper portion 522 of said front portion 506 of said left-side wall 442, as shown in FIG. 36. The purpose of said first round screen vent 438 and said second round screen vent 440 is to allow air movement within said front accessible compartment 468 so that when a patient is being treated the exhaled and inhaled breath flowing into and out of said front accessible compartment 468 is unrestricted.

Said third round screen vent 444 is strategically positioned in the upper portion 524 of said back portion 512 of said right-side wall 436, as shown in FIG. 35. The purpose of said third round screen vent 444 is to allow sufficient air flow into said back inaccessible compartment 470 thereby allowing said ballast 488 cooling system to draw air into and through said ballast 488 for cooling purposes when in operation.

Said first connector 416 connects said mask 412 with said flexible hose 414, as shown in FIG. 34. Said second connector 418 connects said flexible hose 414 with said first end 422 of said right-angle connector 420, as shown in FIG. 34. Said second end 424 of said right-angle 420 is inserted into and through said opening 426 of said top 432 until said second end 424 is well settled within said front accessible compartment 468 of said compartmental container 466 in close proximity with said far-UVC lamp 474. When said second end 424 of said right-angle 420 is removed from said opening 426 of said top 432 an insertable cap 486 is immediately inserted into said opening, as shown in FIG. 41. Said far-UVC lamp 474 and said ballast 488 are electrically connected, as shown in FIG. 39. Said 40-Watt Far UV 222 nm Shatterproof far-UVC lamp 474 penetrates the cell wall of a microorganism and destroys it, but it cannot penetrate the outer layer of human skin or the cornea of the eye.

Said Germicidal UV Light Device 410 is fabricated with but not limited to King Starboard which is composed of High Density Polyethylene (HDPE) and infused with UV inhibitors, meaning it can never rot, delaminate, or fade. One of the best things about said King Starboard is that it's maintenance free. Said King Starboard never needs to be polished or refinished and is easy to clean. Dish soap, citrus cleaners, alcohol, mineral spirits, or erasers are all good options for cleaning of said King Starboard. The actual tensile strength of said King Starboard at yield is over 4,100 PSI. Exposure to the UVC 222 nm wavelength of said far-UVC lamp 474 will have no effect whatsoever on said King Starboard. The slight rise in temperature by said far-UVC lamp 474 when in operation does not create any harmful gases.

Said top 432; said right-side wall 436; said left-side wall 442; said back wall 448; said bottom 450; and said common wall 472 are assembled using stainless fasteners or plastic welding rods. Said door 428 is fastened to one side of said continuous hinge 460 using stainless fasteners and the other side of said continuous hinge 460 is fastened to said bottom 450 of said front accessible compartment 468 using stainless fasteners. Said key locking latch 430 is appropriately centered in the upper portion of said door 428. Said 90° degree Angled Keeper 484 is fastened together with screws to the front center of said top 432 of said front accessible compartment 468 in direct alignment with said key locking latch 430.

The purchased elements used or assembled together and used that are made part of said Germicidal UV Light Device 410 include, said insertable cap 486; said 90° degree Angled Keeper 484; said ballast 488; said far-UVC lamp 474; said detachable AC power cord 446; said first mounting bracket 480; said second mounting bracket 482; said first wire connector 494; said second wire connector 496; said mask 412; said flexible hose 414; said right-angle connector 420; said key locking latch 430; said handle 434; said first round screen vent 438; said second round screen vent 440; said third round screen vent 444; said first self-adhesive anti-skid rubber pad 452; said second self-adhesive anti-skid rubber pad 454; said third self-adhesive anti-skid rubber pad 456; said fourth self-adhesive anti-skid rubber pad 458; said countdown auto shut-off safety outlet 526, such as the SIMPLE TOUCH Auto Shut-Off Safety Outlet; and said continuous hinge 460.

Said first mounting bracket 480 is attached to one end of said far-UVC lamp 474 and said second mounting bracket 482 is attached to the other end of said far-UVC lamp 474. Said far-UVC lamp 474 is located on said common wall 472 of said front accessible compartment 468 approximately three inches down from said top 432 and centrally positioned. The distance between the center of the base of said first mounting bracket 480 and the center of the base of said second mounting bracket 482 are measured and that measurement is used to determine the exact location to drill the two holes into said common wall 472 so that a screw will pass through the drilled holes in the common wall 472 and into the appropriate mounting bracket.

Said ballast 488 is secured, using stainless fasteners, to a raised base and that raised base is attached to said bottom 450 and said common wall 472 in such a way as to position said operational panel 498 through a matched cut-out located near the very bottom of said left-side wall 442 within said back compartment. The two wires coming out of said ballast 488 and the two wires coming out of said far-UVC lamp 474 are appropriately connected with said first wire connector 494 and said second wire connector 496. Said opening 426 of said top 432 has a said insertable cap 486 inserted in it until said Germicidal UV Light Device 410 is going to be used in the administration of a treatment. Said mask 412 is connected to said flexible hose 414. Said flexible hose 414 is then connected to said right-angle connector 420 ready to be connected when needed for a treatment of a patient. Just prior to an administration of treatment to a patient said insertable cap 486 is removed and said second end 424 of said right-angle 420 is snuggly placed through said opening 426 of said top 432 until said second end 424 is well settled within said front accessible compartment 468 of said compartmental container 466 in close proximity with said far-UVC lamp 474.

When in use said Germicidal UV Light Device 410 momentarily captures the exhaled breath of a COVID-19 patient containing active SARS-CoV-2 virions within said front accessible compartment 468 of said Germicidal UV Light Device 410 in which said far-UVC Lamp 474 is mounted, activated, and instantly converts said active SARS-CoV-2 virions to far-UVC inactivated SARS-CoV-2 virions. Within seconds said far-UVC inactivated SARS-CoV-2 virions are inhaled by said COVID-19 patient into the respiratory system of said COVID-19 patient thereby triggering the adaptive immune system which is vital to clearing the SARS-CoV-2 virus. Unlike said active SARS-CoV-2 virions which are able to resist or delay the Dendritic cells (DCs) from capturing them, said far-UVC inactivated SARS-CoV-2 virions do not fight or resist T cells or said Dendritic cells. Said far-UVC inactivated SARS-CoV-2 virions and said active SARS-CoV-2 virions are identical in structure. These facts enable said Dendritic cells to easily capture and present said far-UVC inactivated SARS-CoV-2 virions to the lymphocytes which result in the initiation and regulation of the adaptive immune response. Thus producing the most effective and preferred antibodies.

In a recent study it was found the number of total T cells, $CD4^+$ and $CD8^+$ T cells were dramatically reduced in said COVID-19 patients, especially in patients requiring to be held in an Intensive Care Unit (ICU) care. These T cells were found to appear functionally exhausted. Source: https://www.ncbi.nlm.nih.gov/pmc/articles/PMC7205903/ In some said COVID-19 patients, it is apparent that said SARS-CoV-2 virus is capable of overpowering the immune system of an infected COVID-19 patient thereby impairing the immune system's ability to produce antibodies. For some, their immune system is able to clear said SARS-CoV-2 virus. For others whose immune system is not able to clear said SARS-CoV-2 virus they will most likely experience a fatal outcome. Therefore, early activation of the immune system is paramount to the survival of a person infected with said SARS-CoV-2 virus. There is no way to know at an early enough stage of infection as to whose immune system will clear said SARS-CoV-2 virus and whose immune system will not. The safest thing for a COVID-19 infected person to do is to begin treatments with the Germicidal UV Light Device 410 as soon as you know that you have become infected with said SARS-CoV-2 virus, COVID-19.

Normally, the creation of said far-UVC inactivated SARS-CoV-2 Virion requires a BSL-3 laboratory and would take weeks. All of this is very costly and dangerous. However said Germicidal UV Light Device 410 instantly and safely converts said active SARS-CoV-2 virions to said far-UVC inactivated SARS-CoV-2 virions without the need of a BSL-3 laboratory and associated expenses.

A Prescription for Treatment with said Germicidal UV Light Device 410 must be issued by a Licensed Physician before a treatment with said Germicidal UV Light Device 410 can be administered. Said Licensed Physician or a qualified trained Medical Professional are the only ones that are permitted to administer any type of treatment with said Germicidal UV Light Device 410.

Said qualified trained Medical Professional prior to administering any type of treatment with said Germicidal UV Light Device 410 to a COVID-19 patient must first vet said COVID-19 patient in the following manner: a qualified trained Medical Professional wearing gloves, gown, face shield and a N95 respirator acquires the medical chart of said COVID-19 patient; said qualified trained Medical Professional reviews said medical chart of said COVID-19 patient; said qualified trained Medical Professional finds that said COVID-19 patient has not taken an expectorant over the last 24 hours; said qualified trained Medical Professional continues to review said medical chart of said COVID-19 patient; said qualified trained Medical Professional finds that said COVID-19 patient has not taken any cough suppressants over the last 24 hours; said qualified trained Medical Professional continues further to review said medical chart of said COVID-19 patient; said qualified trained Medical Professional finds that a Prescription for Treatment with said Germicidal UV Light Device has been issued by a Licensed Physician; said qualified trained Medical Professional writes on said medical chart of said COVID-19 patient Approved for Treatment with said Germicidal UV Light Device; said qualified trained Medical Professional writes the date approved; said qualified trained Medical Professional initials his writings; and said qualified trained Medical Professional returns the medical chart of said COVID-19 patient.

Once said vetting process has been completed said Licensed Physician or said qualified trained Medical Professional may administer a prescribed Consecutive Breathing Treatment with said Germicidal UV Light Device 410 to a COVID-19 patient in the following manner: a qualified trained Medical Professional wearing gloves, gown, face shield and a N95 respirator acquires the medical chart of said COVID-19 patient; said qualified trained Medical Professional reviews said medical chart of said COVID-19 patient and finds that said COVID-19 patient is approved for a Consecutive Breathing Treatment with said Germicidal UV Light Device; said qualified trained Medical Professional acquires said Germicidal UV Light Device from the appropriate storage area; said qualified trained Medical Professional transports said Germicidal UV Light Device to said COVID-19 patients room; said qualified trained Medical Professional removes the 'Ready for Use!' tag from the handle of said Germicidal UV Light Device; said qualified trained Medical Professional removes an insertable cap from an opening on the top of the accessible compartment of said Germicidal UV Light Device; said qualified trained Medical Professional acquires an already connected mask, flexible hose, and right-angle connector; said qualified trained Medical Professional installs said already connected mask, said flexible hose, and said right-angle connector into said opening on said top of said accessible compartment by pushing the second end of said right-angle connector into and through said opening; said qualified trained Medical Professional removes the detachable AC power cord and attached countdown auto shut-off safety outlet from said handle; said qualified trained Medical Professional inserts three-prong receptacle of said detachable AC power cord fully upon the three-prong male connector of the operational panel of a Ballast; said qualified trained Medical Professional plugs in said countdown auto shut-off safety outlet having an already inserted plug of said detachable AC power cord into the nearest three hole electrical wall socket; said qualified trained Medical Professional acquires said COVID-19 patients Prescription for Treatment with said Germicidal UV Light Device; said qualified trained Medical Professional reviews said COVID-19 patients said Prescription of Treatment and acquires said Consecutive Breathing Treatment plan which is two five minute treatments per day for two consecutive days; said qualified trained Medical Professional raises the upper trunk of said COVID-19 patient; said qualified trained Medical Professional tells said COVID-19 patient that said qualified trained Medical Professional will hold said mask in place over both nostrils and mouth during treatment; said qualified trained Medical Professional instructs said COVID-19 patient that said qualified trained Medical Professional will instruct when to exhale and when to inhale during said treatment; said qualified trained Medical Professional switches the ON and OFF switch to the ON position; said qualified trained Medical Professional sets said countdown auto shut-off safety outlet to the five minute countdown marker; said qualified trained Medical Professional acquires said mask; said qualified trained Medical Professional holds said mask in position over the mouth and nostrils of said COVID-19 patient; said qualified trained Medical Professional instructs said COVID-19 patient to exhale forcefully and completely into said mask; said qualified trained Medical Professional instructs said COVID-19 patient to inhale deeply and slowly through said mask; said qualified trained Medical Professional continues to instruct said COVID-19 patient when to exhale and when to inhale until the said countdown auto shut-off safety outlet shuts off the electrical flow to said Germicidal UV Light Device; said qualified trained Medical Professional removes said mask from said COVID-19 patient; said qualified trained Medical Professional switches said ON and OFF switch to the OFF position; said qualified trained Medical Professional evaluates said COVID-19 patient; said qualified trained Medical Professional instructs said COVID-19 patient to remain elevated for a period of 30 minutes; said qualified trained Medical Professional removes said already connected mask, said flexible hose, and said right-angle connector from said opening by pulling said second end of said right-angle connector out of said opening; said qualified trained Medical Professional places said already connected mask, said flexible hose, and said right-angle connector into a pouch; said qualified trained Medical Professional seals said pouch; said qualified trained Medical Professional inserts said insertable cap into said opening of said top of said accessible compartment; said qualified trained Medical Professional unplugs said countdown auto shut-off safety outlet from said three hole electrical wall socket; said qualified trained Medical Professional unplugs said three-prong receptacle of said detachable AC power cord from said three-prong male connector of said operational panel of said Ballast; said qualified trained Medical Professional wraps up said detachable AC power cord and attached said countdown auto shut-off safety outlet; said qualified trained Medical Professional secures said detachable AC power cord and said attached countdown auto shut-off safety outlet to said handle of said Germicidal UV Light Device; said qualified trained Medical Professional acquires said COVID-19 patients medical chart; said qualified trained Medical Professional writes the date and time that said COVID-19 patient completed the first five minute treatment of said Consecutive Breathing Treatment on said COVID-19 patients medical chart; said qualified trained Medical Professional writes on the said COVID-19 patients medical chart the scheduled time of the second five minutes of said Consecutive Breathing Treatment and all subsequent treatments according to said Prescription for Treatment; said qualified trained Medical Professional initials his writings on said COVID-19 patients medical chart; said qualified trained Medical Professional takes said pouch to the nearest Hazmat Drop Box; said qualified trained Medical Professional drops said pouch into said nearest Hazmat Drop Box; said qualified trained Medical Professional takes the remaining part of said Germicidal UV Light Device to the Make Ready Area; said qualified trained Medical Professional removes said gown, said face shield, said N95 respirator and said gloves; and said qualified trained Medical Professional deposits said gown, and said face shield, said N95 respirator and said gloves into the nearest Hazmat Drop Box.

Once said vetting process has been completed, said Licensed Physician or said qualified trained Medical Professional may administer a prescribed Intermittent Breathing Treatment with said Germicidal UV Light Device 410 to a COVID-19 patient in the following manner: a qualified trained Medical Professional wearing gloves, gown, face shield and a N95 respirator acquires the medical chart of said COVID-19 patient; said qualified trained Medical Professional reviews said medical chart of said COVID-19 patient and finds that said COVID-19 patient is approved for Intermittent Breathing Treatment with said Germicidal UV Light Device; said qualified trained Medical Professional acquires said Germicidal UV Light Device from the appropriate storage area; said qualified trained Medical Professional transports said Germicidal UV Light Device to said COVID-19 patients room; said qualified trained Medical Professional removes the 'Ready for Use!' tag from the handle of said Germicidal UV Light Device; said qualified trained Medical Professional removes an insertable cap from an opening on the top of the accessible compartment of said Germicidal UV Light Device; said qualified trained Medical Professional acquires an already connected mask, flexible hose, and right-angle connector; said qualified trained Medical Professional installs said already connected mask, said flexible hose, and said right-angle connector by pushing the second end of said right-angle connector into and through said opening on said top of said accessible compartment; said qualified trained Medical Professional removes the detachable AC power cord and attached countdown auto shut-off safety outlet from said handle; said qualified trained Medical Professional inserts three-prong receptacle of said detachable AC power cord fully upon the three-prong male connector of the operational panel of a Ballast; said qualified trained Medical Professional plugs in said countdown auto shut-off safety outlet having an already inserted plug of said detachable AC power cord into the nearest three hole electrical wall socket; said qualified trained Medical Professional acquires said COVID-19 patients Prescription for Treatment with said Germicidal UV Light Device; said qualified trained Medical Professional reviews said COVID-19 patients said Prescription of Treatment and acquires the type of treatment which is two five minute Intermittent Breathing Treatments per day for two consecutive days; said qualified trained Medical Professional raises the upper trunk of said COVID-19 patient in preparation for said COVID-19 patient to receive treatment with said Germicidal UV Light Device; said qualified trained Medical Professional tells said COVID-19 patient that said qualified trained Medical Professional will hold said mask in place over both nostrils and mouth during treatment; said qualified trained Medical Professional instructs said COVID-19 patient that said qualified trained Medical Professional will instruct when to exhale and when to inhale during said treatment; said qualified trained Medical Professional switches the ON and OFF switch to the ON position; said qualified trained Medical Professional sets said countdown auto shut-off safety outlet to the five minute countdown marker; said qualified trained Medical Professional acquires said mask; said qualified trained Medical Professional holds said mask in position over the mouth and nostrils of said COVID-19 patient; said qualified trained Medical Professional instructs said COVID-19 patient to exhale forcefully and completely into said mask; said qualified trained Medical Professional takes note of the exact time that said COVID-19 patient was told to exhale forcefully and completely into said mask; said qualified trained Medical Professional removes said mask from said mouth and said nostrils of said COVID-19 patient; said qualified trained Medical Professional waits 20 seconds; said qualified trained Medical Professional acquires said mask; said qualified trained Medical Professional holds said mask over said mouth and said nostrils of said COVID-19 patient; said qualified trained Medical Professional instructs said COVID-19 patient to inhale deeply and slowly through said mask; said qualified trained Medical Professional continues to instruct said COVID-19 patient when to exhale and when to inhale until the said countdown auto shut-off safety outlet shuts off the electrical flow to said Germicidal UV Light Device; said qualified trained Medical Professional removes said mask from said COVID-19 patient; said qualified trained Medical Professional switches said ON and OFF switch to the OFF position; said qualified trained Medical Professional evaluates said COVID-19 patient; said qualified trained Medical Professional instructs said COVID-19 patient to remain elevated for a period of 30 minutes; said qualified trained Medical Professional removes said already connected mask, said flexible hose, and said right-angle connector from said opening by pulling the said second end of said right-angle connector out of said opening; said qualified trained Medical Professional places said already connected mask, said flexible hose, and said right-angle connector into a pouch; said qualified trained Medical Professional seals said pouch; said qualified trained Medical Professional inserts said insertable cap into said opening of said top of said accessible compartment; said qualified trained Medical Professional unplugs said countdown auto shut-off safety outlet from said three hole electrical wall socket; said qualified trained Medical Professional unplugs said three-prong receptacle of said detachable AC power cord from said three-prong male connector of said operational panel of said Ballast; said qualified trained Medical Professional wraps said detachable AC power cord and attached said countdown auto shut-off safety outlet up; said qualified trained Medical Professional secures said detachable AC power cord and attached said countdown auto shut-off safety outlet to said handle of said Germicidal UV Light Device; said qualified trained Medical Professional acquires said COVID-19 patients medical chart; said qualified trained Medical Professional writes the date and time that said COVID-19 patient completed said the first five minutes of said Intermittent Breathing Treatment on said COVID-19 patients medical chart; said qualified trained Medical Professional writes on the said COVID-19 patients medical chart the scheduled time of the second five minutes of said Intermittent Breathing Treatment and all subsequent treatments according to said Prescription for Treatment; said qualified trained Medical Professional initials his writings on said COVID-19 patients medical chart; said qualified trained Medical Professional takes said pouch to the nearest Hazmat Drop Box; said qualified trained Medical Professional drops said pouch into said nearest Hazmat Drop Box; said qualified trained Medical Professional takes the remaining part of said Germicidal UV Light Device to the Make Ready Area; said qualified trained Medical Professional removes said gown, said face shield, said N95 respirator and said gloves; and said qualified trained Medical Professional deposits said gown, said face shield, said N95 respirator and said gloves into the nearest Hazmat Drop Box.

Prior to a Prescription for Treatment with the Germicidal UV Light Device 410 being issued by a Licensed Physician and during the examination of a COVID-19 patient, said COVID-19 Patient was asked to participate in a Creation and Collection Program which involves breathing into said Germicidal Light Device 410 for the creation of far-UVC SARS-CoV-2 virions prior to receiving any treatment with said Germicidal Light Device 410. Said COVID-19 Patients reply is noted on said Prescription of Treatment with said Germicidal Light Device 410. Following the administration of said Creation and Collection Program to said COVID-19 Patient, said qualified trained Medical Professional will always immediately administer said Prescription for Treatment with the Germicidal UV Light Device 410 to said COVID-19 Patient.

Said far-UVC inactivated SARS-CoV-2 virions can be collected and processed further in combination with an adjuvant which will enable Vaccine Injections for Front Line Workers and others. Although said far-UVC inactivated SARS-CoV-2 virions can be collected from the front accessible compartment 468 of said Germicidal UV Light Device 410 immediately after a treatment has been administered to said COVID-19 patient, a much greater volume of said far-UVC inactivated SARS-CoV-2 virions can be created and collected from said front accessible compartment 468 of said Germicidal UV Light Device 410 when said COVID-19 patient participates in said Creation and Collection Program.

On said Prescription of Treatment with said Germicidal Light Device of said COVID-19 patient it has been noted that said COVID-19 patient agreed to participate in said Creation and Collection Program. Said Licensed Physician or said qualified trained Medical Professional may administer said Creation and Collection Program with said Germicidal UV Light Device 410 to said COVID-19 patient in the following manner: a qualified trained Medical Professional wearing gloves, gown, face shield and a N95 respirator acquires the medical chart of said COVID-19 patient; said qualified trained Medical Professional reviews said medical chart of said COVID-19 patient and finds that said COVID-19 patient is approved for participation in said Creation and Collection Program; said qualified trained Medical Professional acquires said Germicidal UV Light Device from the appropriate storage area; said qualified trained Medical Professional transports said Germicidal UV Light Device to said COVID-19 patients room; said qualified trained Medical Professional removes the Ready to Use! Tag from the handle of said Germicidal UV Light Device; said qualified trained Medical Professional removes an insertable cap from an opening of top of accessible compartment of said Germicidal UV Light Device; said qualified trained Medical Professional acquires an already connected mask, flexible hose, and right-angle connector; said qualified trained Medical Professional installs said already connected mask, said flexible hose, and said right-angle connector by pushing the second end of said right-angle connector into and through said opening; said qualified trained Medical Professional removes the detachable AC power cord and attached countdown auto shut-off safety outlet from said handle; said qualified trained Medical Professional inserts three-prong receptacle of said detachable AC power cord fully upon the three-prong male connector of the operational panel of a Ballast; said qualified trained Medical Professional plugs in said countdown auto shut-off safety outlet having an already inserted plug of said detachable AC power cord into the nearest three hole electrical wall socket; said qualified trained Medical Professional raises the upper trunk of said COVID-19 patient; said qualified trained Medical Professional tells said COVID-19 patient that said qualified trained Medical Professional will hold said mask in place over both nostrils and mouth during treatment; said qualified trained Medical Professional instructs said COVID-19 patient that said qualified trained Medical Professional will instruct when to exhale; said qualified trained Medical Professional switches the ON and OFF switch to the ON position; said qualified trained Medical Professional sets said countdown auto shut-off safety outlet to the five minute countdown marker; said qualified trained Medical Professional acquires said mask; said qualified trained Medical Professional holds said mask in position over the mouth and nostrils of said COVID-19 patient; said qualified trained Medical Professional instructs said COVID-19 patient to exhale forcefully and completely into said mask; said qualified trained Medical Professional removes said mask from said mouth and said nostrils of said COVID-19 patient; said qualified trained Medical Professional switches said ON and OFF switch to the OFF position; said qualified trained Medical Professional evaluates said COVID-19 patient; said qualified trained Medical Professional removes said already connected mask, said flexible hose, and said right-angle connector from said opening by pulling said second end of said right-angle connector out of said opening; said qualified trained Medical Professional places said already connected mask, said flexible hose, and said right-angle connector into a pouch; said qualified trained Medical Professional seals said pouch; said qualified trained Medical Professional inserts said insertable cap into said opening of said top of said accessible compartment; said qualified trained Medical Professional acquires a three inch wide roll of self-adhesive tape; said qualified trained Medical Professional cuts a piece of four inch tape from said three inch wide roll of self-adhesive tape; said qualified trained Medical Professional secures said piece of four inch tape from said three inch wide roll of self-adhesive tape over first round screen vent of the upper portion of front portion of right-side wall; said qualified trained Medical Professional acquires a three inch wide roll of self-adhesive tape; said qualified trained Medical Professional cuts a piece of four inch tape from said three inch wide roll of self-adhesive tape; said qualified trained Medical Professional secures said piece of four inch tape from said three inch wide roll of self-adhesive tape over first round screen vent of the upper portion of front portion of left-side wall; said qualified trained Medical Professional switches said ON and OFF switch to the ON position; said qualified trained Medical Professional takes note of the exact time that said ON and OFF switch was switched to said ON position; said qualified trained Medical Professional at the end of one minute from the time that said ON and OFF switch was switched to said ON position switches said ON and OFF switch to the OFF position; said qualified trained Medical Professional unplugs said countdown auto shut-off safety outlet from said three hole electrical wall socket; said qualified trained Medical Professional unplugs said three-prong receptacle of said detachable AC power cord from said three-prong male connector of said operational panel of said Ballast; said qualified trained Medical Professional wraps said detachable AC power cord and attached said countdown auto shut-off safety outlet up; said qualified trained Medical Professional secures said detachable AC power cord and attached said countdown auto shut-off safety outlet to said handle of said Germicidal UV Light Device; said qualified trained Medical Professional acquires said COVID-19 patient said medical chart; said qualified trained Medical Professional writes the date and time that said COVID-19 patient completed participation in said Creation and Collection Program on said COVID-19 patients medical chart; said qualified trained Medical Professional initials his writings on said COVID-19 patients medical chart; said qualified trained Medical Professional takes said pouch to the nearest Hazmat Drop Box; said qualified trained Medical Professional drops said pouch into said nearest Hazmat Drop Box; said qualified trained Medical Professional takes the remaining part of said Germicidal UV Light Device to the Make Ready Area; said qualified trained Medical Professional removes said gown, said face shield, said N95 respirator and said gloves; and said qualified trained Medical Professional deposits said gown, said face shield, said N95 respirator and said gloves into the nearest Hazmat Drop Box.

The collection of far-UVC inactivated SARS-CoV-2 Virions from said accessible compartment of said Germicidal UV Light Device 410 for further processing is done immediately following said COVID-19 patient participation in said Creation and Collection Program or any other treatment made with the said Germicidal UV Light Device 410 to Make Ready for Use in the following manner: a qualified trained Medical Professional wearing gloves, gown, face shield and a N95 respirator acquires from the Make Ready Area a Germicidal UV Light Device recently used; said qualified trained Medical Professional inspects the outside surfaces of said Germicidal UV Light Device; said qualified trained Medical Professional lightly wipes said outside surfaces of said Germicidal UV Light Device with 70% ethyl alcohol disinfectant wipes; said qualified trained Medical Professional removes the detachable AC power cord and attached countdown auto shut-off safety outlet from the handle of said Germicidal UV Light Device; said qualified trained Medical Professional inserts three-prong receptacle of said detachable AC power cord fully upon the three-prong male connector of the operational panel of a Ballast; said qualified trained Medical Professional plugs in said countdown auto shut-off safety outlet having an already inserted plug of said detachable AC power cord into the nearest three hole electrical wall socket; said qualified trained Medical Professional switches said ON and OFF switch to the ON position; said qualified trained Medical Professional takes note of the time that said ON and OFF switch was switched to said ON position; said qualified trained Medical Professional switches said ON and OFF switch to the OFF position after 30 seconds have elapsed; said qualified trained Medical Professional unplugs said countdown auto shut-off safety outlet from said three hole electrical wall socket; said qualified trained Medical Professional unplugs said three-prong receptacle of said detachable AC power cord from said three-prong male connector of said operational panel of said Ballast; said qualified trained Medical Professional lightly wipes said detachable AC power cord and said countdown auto shut-off safety outlet with 70% ethyl alcohol disinfectant wipes; said qualified trained Medical Professional wraps up said detachable AC power cord and attached said countdown auto shut-off safety outlet; said qualified trained Medical Professional secures said detachable AC power cord and attached said countdown auto shut-off safety outlet to said handle of said Germicidal UV Light Device; said qualified trained Medical Professional removes said insertable cap from the opening on top of said Germicidal UV Light Device; said qualified trained Medical Professional collects said far-UVC inactivated SARS-CoV-2 virions through said opening on said top of said Germicidal UV Light Device into a container; said qualified trained Medical Professional seals said container; said qualified trained Medical Professional sends said container to the Laboratory for further processing; said qualified trained Medical Professional unlocks the door of said Germicidal UV Light Device; said qualified trained Medical Professional opens said door of said Germicidal UV Light Device; said qualified trained Medical Professional extracts said far-UVC inactivated SARS-CoV-2 virions from the inside surfaces of said accessible compartment of said Germicidal UV Light Device; said qualified trained Medical Professional sends said extracted far-UVC inactivated SARS-CoV-2 virions to said Laboratory for further processing; said qualified trained Medical Professional inspects the said accessible compartment of said Germicidal UV Light Device; said qualified trained Medical Professional inspects the Germicidal Lamp within said accessible compartment; said qualified trained Medical Professional lightly wipes said inside surfaces of said Germicidal UV Light Device with 70% ethyl alcohol disinfectant wipes; said qualified trained Medical Professional lightly wipes said Germicidal Lamp within said accessible compartment; said qualified trained Medical Professional lightly wipes said opening of said Germicidal UV Light Device with 70% ethyl alcohol disinfectant wipes; said qualified trained Medical Professional installs a new insertable cap into said opening of said Germicidal UV Light Device; said qualified trained Medical Professional closes said door of said accessible compartment; said qualified trained Medical Professional locks said door of said accessible compartment; said qualified trained Medical Professional acquires a 'Ready for Use!' tag; said qualified trained Medical Professional writes the date of inspection and the initials of said qualified trained Medical Professional on said 'Ready for Use!' tag; said qualified trained Medical Professional attached said 'Make Ready Tag' onto said handle of said Germicidal UV Light Device; said qualified trained Medical Professional places said Germicidal UV Light Device in the appropriate storage area; said qualified trained Medical Professional removes said gloves, said gown, said face shield and said N95 respirator; and said qualified trained Medical Professional places said gloves, said gown, said face shield, said N95 respirator and said insertable cap into a nearby Hazmat Drop Box.

When said Prescription for Treatment with said Germicidal UV Light Device 410 requires an initial five minute Consecutive Breathing Treatment and a subsequent said five minute Consecutive Breathing Treatment, the said subsequent five minute Consecutive Breathing Treatment are administered in the following manner: a qualified trained Medical Professional wearing gloves, gown, face shield and a N95 respirator acquires the medical chart of the COVID-19 patient; said qualified trained Medical Professional reviews said medical chart of said COVID-19 patient and finds that said COVID-19 patient is approved for a subsequent five minute Consecutive Breathing Treatment with said Germicidal UV Light Device; said qualified trained Medical Professional acquires said Germicidal UV Light Device from the appropriate storage area; said qualified trained Medical Professional transports said Germicidal UV Light Device to said COVID-19 patients room; said qualified trained Medical Professional removes the 'Ready for Use!' tag from the handle of said Germicidal UV Light Device; said qualified trained Medical Professional removes an insertable cap from an opening on the top of the accessible compartment of said Germicidal UV Light Device; said qualified trained Medical Professional acquires an already connected mask, flexible hose, and right-angle connector; said qualified trained Medical Professional installs said already connected mask, said flexible hose, and said right-angle connector opening on said top of said accessible compartment by pushing the second end of said right-angle connector into and through said opening; said qualified trained Medical Professional removes the detachable AC power cord and attached countdown auto shut-off safety outlet from said handle; said qualified trained Medical Professional inserts three-prong receptacle of said detachable AC power cord fully upon the three-prong male connector of the operational panel of a Ballast; said qualified trained Medical Professional plugs in said countdown auto shut-off safety outlet having an already inserted plug of said detachable AC power cord into the nearest three hole electrical wall socket; said qualified trained Medical Professional raises the upper trunk of said COVID-19 patient; said qualified trained Medical Professional tells said COVID-19 patient that said qualified trained Medical Professional will hold said mask in place over both nostrils and mouth during treatment; said qualified trained Medical Professional instructs said COVID-19 patient that said qualified trained Medical Professional will instruct when to exhale and when to inhale during said treatment; said qualified trained Medical Professional switches the ON and OFF switch to the ON position; said qualified trained Medical Professional sets said countdown auto shut-off safety outlet to the five minute countdown marker; said qualified trained Medical Professional acquires said mask; said qualified trained Medical Professional holds said mask in position over the mouth and nostrils of said COVID-19 patient; said qualified trained Medical Professional instructs said COVID-19 patient to exhale forcefully and completely into said mask; said qualified trained Medical Professional instructs said COVID-19 patient to inhale deeply and slowly through said mask; said qualified trained Medical Professional continues to instruct said COVID-19 patient when to exhale and when to inhale until the said countdown auto shut-off safety outlet shuts off the electrical flow to said Germicidal UV Light Device; said qualified trained Medical Professional removes said mask from said COVID-19 patient; said qualified trained Medical Professional switches said ON and OFF switch to the OFF position; said qualified trained Medical Professional evaluates said COVID-19 patient; said COVID-19 patient instructs said COVID-19 patient to remain elevated for a period of 30 minutes; said qualified trained Medical Professional removes said already connected mask, said flexible hose, and said right-angle connector from said opening by pulling said second end of said right-angle connector out of said opening; said qualified trained Medical Professional places said already connected mask, said flexible hose, and said right-angle connector into a pouch; said qualified trained Medical Professional seals said pouch; said qualified trained Medical Professional inserts said insertable cap into said opening on said top of said accessible compartment; said qualified trained Medical Professional unplugs said countdown auto shut-off safety outlet from said three hole electrical wall socket; said qualified trained Medical Professional unplugs said three-prong receptacle of said detachable AC power cord from said three-prong male connector of said operational panel of said Ballast; said qualified trained Medical Professional wraps up said detachable AC power cord and attached said countdown auto shut-off safety outlet; said qualified trained Medical Professional secures said detachable AC power cord and attached said countdown auto shut-off safety outlet to said handle of said Germicidal UV Light Device; said qualified trained Medical Professional acquires said COVID-19 patients medical chart; said qualified trained Medical Professional writes the date and time that said COVID-19 patient completed the subsequent five minute treatment of said Consecutive Breathing Treatment on said COVID-19 patients medical chart; said qualified trained Medical Professional initials his writings on said COVID-19 patients medical chart; said qualified trained Medical Professional takes said pouch to the nearest Hazmat Drop Box; said qualified trained Medical Professional drops said pouch into said nearest Hazmat Drop Box; said qualified trained Medical Professional takes the remaining part of said Germicidal UV Light Device to the Make Ready Area; said qualified trained Medical Professional removes said gown, said face shield, said N95 respirator and said gloves; and said qualified trained Medical Professional deposits said gown, and said face shield, said N95 respirator and said gloves into the nearest Hazmat Drop Box.

When said Prescription for Treatment with said Germicidal UV Light Device 410 requires an initial five minute said Intermittent Breathing Treatment and a subsequent five minute said Intermittent Breathing Treatment, the said subsequent five minute Intermittent Breathing Treatment are administered in the following manner: a qualified trained Medical Professional wearing gloves, gown, face shield and a N95 respirator acquires the medical chart of the COVID-19 patient; said qualified trained Medical Professional reviews said medical chart of said COVID-19 patient and finds that said COVID-19 patient is approved for a subsequent five minute said Intermittent Breathing Treatment with said Germicidal UV Light Device; said qualified trained Medical Professional acquires said Germicidal UV Light Device from the appropriate storage area; said qualified trained Medical Professional transports said Germicidal UV Light Device to said COVID-19 patients room; said qualified trained Medical Professional removes the 'Ready for Use!' tag from the handle of said Germicidal UV Light Device; said qualified trained Medical Professional removes an insertable cap from an opening on the top of the accessible compartment of said Germicidal UV Light Device; said qualified trained Medical Professional acquires an already connected mask, flexible hose, and right-angle connector; said qualified trained Medical Professional installs said already connected mask, said flexible hose, and said right-angle connector into said opening on said top of said accessible compartment by pushing the second end of said right-angle connector into and through said opening; said qualified trained Medical Professional removes the detachable AC power cord and attached countdown auto shut-off safety outlet from said handle; said qualified trained Medical Professional inserts three-prong receptacle of said detachable AC power cord fully upon the three-prong male connector of the operational panel of a Ballast; said qualified trained Medical Professional plugs in said countdown auto shut-off safety outlet having an already inserted plug of said detachable AC power cord into the nearest three hole electrical wall socket; said qualified trained Medical Professional raises the upper trunk of said COVID-19 patient; said qualified trained Medical Professional tells said COVID-19 patient that said qualified trained Medical Professional will hold said mask in place over both nostrils and mouth during treatment; said qualified trained Medical Professional instructs said COVID-19 patient that said qualified trained Medical Professional will instruct when to exhale and when to inhale during said treatment; said qualified trained Medical Professional switches the ON and OFF switch to the ON position; said qualified trained Medical Professional sets said countdown auto shut-off safety outlet to the five minute countdown marker; said qualified trained Medical Professional acquires said mask; said qualified trained Medical Professional holds said mask in position over the mouth and nostrils of said COVID-19 patient; said qualified trained Medical Professional instructs said COVID-19 patient to exhale forcefully and completely into said mask; said qualified trained Medical Professional takes note of the exact time that said COVID-19 patient was told to exhale forcefully and completely into said mask; said qualified trained Medical Professional removes said mask from said mouth and said nostrils of said COVID-19 patient; said qualified trained Medical Professional waits 20 seconds; said qualified trained Medical Professional acquires said mask; said qualified trained Medical Professional holds said mask over said mouth and said nostrils of said COVID-19 patient; said qualified trained Medical Professional instructs said COVID-19 patient to inhale deeply and slowly through said mask; said qualified trained Medical Professional continues to instruct said COVID-19 patient when to exhale and when to inhale until the said countdown auto shut-off safety outlet shuts off the electrical flow to said Germicidal UV Light Device; said qualified trained Medical Professional removes said mask from said COVID-19 patient; said qualified trained Medical Professional switches said ON and OFF switch to the OFF position; said qualified trained Medical Professional evaluates said COVID-19 patient; said COVID-19 patient instructs said COVID-19 patient to remain elevated for a period of 30 minutes; said qualified trained Medical Professional removes said already connected mask, said flexible hose, and said right-angle connector from said opening by pulling said second end of said right-angle connector out of said opening; said qualified trained Medical Professional places said already connected mask, said flexible hose, and said right-angle connector into a pouch; said qualified trained Medical Professional seals said pouch; said qualified trained Medical Professional inserts said insertable cap into said opening on said top of said accessible compartment; said qualified trained Medical Professional unplugs said countdown auto shut-off safety outlet from said three hole electrical wall socket; said qualified trained Medical Professional unplugs said three-prong receptacle of said detachable AC power cord from said three-prong male connector of said operational panel of said Ballast; said qualified trained Medical Professional wraps up said detachable AC power cord and attached said countdown auto shut-off safety outlet; said qualified trained Medical Professional secures said detachable AC power cord and attached said countdown auto shut-off safety outlet to said handle of said Germicidal UV Light Device; said qualified trained Medical Professional acquires said COVID-19 patients medical chart; said qualified trained Medical Professional writes the date and time that said COVID-19 patient completed the said subsequent five minute Intermittent Breathing Treatment on said COVID-19 patients medical chart; said qualified trained Medical Professional initials his writings on said COVID-19 patients medical chart; said qualified trained Medical Professional takes said pouch to the nearest Hazmat Drop Box; said qualified trained Medical Professional drops said pouch into said nearest Hazmat Drop Box; said qualified trained Medical Professional takes the remaining part of said Germicidal UV Light Device to the Make Ready Area; said qualified trained Medical Professional removes said gown, said face shield, said N95 respirator and said gloves; and said qualified trained Medical Professional deposits said gown, and said face shield, said N95 respirator and said gloves into the nearest Hazmat Drop Box.

Basically the main purpose of said Germicidal UV Light Device 410 when in operation is as follows: an exhaled breath of a COVID 19 patient containing active SARS-CoV-2 virions is received within said accessible compartment, where an activated said electrically powered far-UVC germicidal lamp within seconds changes said active SARS-CoV-2 virions into a far-UVC inactivated SARS-CoV-2 virions which are carried by the next inhaled breath of said COVID 19 patient into the respiratory system wherein the immune system becomes activated to produce antibodies once the said far-UVC inactivated SARS-CoV-2 virion(s) are captured by the Dendritic cells (DCs) and presented to lymphocytes.

While the present invention has been described in connection with the preferred embodiments of the various figures, it is to be understood that other similar embodiments may be used, or modifications and additions may be made to the described embodiment for performing the same function of the present invention without deviating therefrom. Therefore, the present invention should not be limited to any single embodiment, but rather construed in breadth and scope in accordance with the recitation of the appended claims.

I claim:

1. An apparatus, comprising:
a housing;
an accessible compartment of said housing;
an inaccessible compartment of said housing;
an at least one screened opening of said accessible compartment;
an at least one screened opening of said inaccessible compartment;
an access door of said accessible compartment;
an electrically powered far-UVC germicidal lamp mounted within said accessible compartment;
a ballast of sufficient power to power said electrically powered far-UVC germicidal lamp mounted partially within said inaccessible compartment;
a connector of said ballast that connects to receive an electrical current;
an ON and OFF switch of said ballast that controls received electrical current;
an AC power cord connected to said connector of said ballast at one end and connected to an electrical outlet at the other end;
said far-UVC germicidal lamp and said ballast are electrically connected;
a sufficient power supply to electrically power said far-UVC germicidal lamp;
an opening in said accessible compartment, positionally located in close proximity to said far-UVC germicidal lamp;
an at least one hollow right-angle connector;
a first connected and a second connector;
a particular end of said at least one hollow right-angle connector is inserted into and through said opening of said accessible compartment;
a connectable mask having an unrestricted bidirectional air passageway;
a hollow connectable flexible tube;
said connectable mask, said first connector, said hollow connectable flexible tube, said second connector and said hollow right-angle connector are consecutively assembled together for use;
said electrically powered far-UVC germicidal lamp is configured to convert within seconds an active infectious virion(s) from exhaled breath of an infected person, when in use, into a far-UVC inactivated virion(s) for the purpose of being immediately inhaled by the person wherein said far-UVC inactivated virion(s) are captured by Dendritic cells (DCs) and presented to lymphocytes to initiate and regulate the person's adaptive immune response; and
wherein said electrically powered far-UVC germicidal lamp mounted within said accessible compartment stands ready to convert an active live SARS-CoV-2 virion into a far-UVC inactivated SARS-CoV-2 virion.

2. The apparatus of claim 1 further comprising a countdown auto shut-off safety outlet connected in between said electrical outlet and said AC power cord.

3. The apparatus of claim 1 further comprising a key locking latch for said access door.

4. The apparatus of claim 1 further comprising said far-UVC germicidal lamp having a specific wavelength of 222 nanometers.

5. The apparatus of claim 1 further comprising said far-UVC germicidal lamp having a specific wavelength of 253.7 nanometers.

6. The apparatus of claim 1 further comprising a hinge connected to said access door and said accessible compartment.

7. The apparatus of claim 1 further comprising at least one anti-skid rubber pad secured to the bottom outer surface of said housing.

8. The apparatus of claim 1 further comprising an insertable cap.

9. The apparatus of claim 1 wherein said housing is a vented container.

* * * * *